US012157801B2

(12) United States Patent
Zhao et al.

(10) Patent No.: US 12,157,801 B2
(45) Date of Patent: Dec. 3, 2024

(54) STRONG ADHESION OF CONDUCTING POLYMERS ON DIVERSE SUBSTRATES

(71) Applicant: Massachusetts Institute of Technology, Cambridge, MA (US)

(72) Inventors: Xuanhe Zhao, Allston, MA (US); Hyunwoo Yuk, Cambridge, MA (US); Akihisa Inoue, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 500 days.

(21) Appl. No.: 16/866,584

(22) Filed: May 5, 2020

(65) Prior Publication Data

US 2020/0377677 A1    Dec. 3, 2020

Related U.S. Application Data

(60) Provisional application No. 62/853,785, filed on May 29, 2019.

(51) Int. Cl.
| | |
|---|---|
| C08J 5/12 | (2006.01) |
| A61L 27/34 | (2006.01) |
| A61L 31/10 | (2006.01) |
| C08L 75/04 | (2006.01) |
| C08L 101/12 | (2006.01) |
| C09J 9/00 | (2006.01) |
| C09J 175/04 | (2006.01) |
| C25D 9/02 | (2006.01) |

(52) U.S. Cl.
CPC .............. *C08J 5/122* (2013.01); *A61L 27/34* (2013.01); *A61L 31/10* (2013.01); *C08J 5/124* (2013.01); *C08L 75/04* (2013.01); *C08L 101/12* (2013.01); *C09J 9/00* (2013.01); *C09J 175/04* (2013.01); *A61L 2420/02* (2013.01); *A61L 2420/08* (2013.01); *C08J 2300/208* (2013.01); *C25D 9/02* (2013.01)

(58) Field of Classification Search
CPC ...... C08J 5/122; C08J 5/124; C08J 2300/208; C08L 75/04; C08L 101/12; C09J 9/00; C09J 175/04; C25D 9/02; A61L 31/10; A61L 27/34; A61L 2420/02; A61L 2420/08
See application file for complete search history.

(56) References Cited

U.S. PATENT DOCUMENTS

| | | | | |
|---|---|---|---|---|
| 5,849,368 A | * | 12/1998 | Hostettler | ................ C08J 7/056 427/539 |
| 2012/0123527 A1 | * | 5/2012 | Isch | ........................ A61L 31/10 623/1.35 |

OTHER PUBLICATIONS

Sungchul, et al "Thin Film hydrophilic electroactive polymer coatings for bioelectrodes": Journal of Materials Chemistry B, vol. 1, No. 31, Jan. 1, 2013, p. 3803.

Heo Dong Nyoung, et al: "Multifunctional hydrogel coatings on the surface of neural cuff electrode for improving electrode-nerve tissue interfaces"; ACTA Biomaterialia Elsevier, Amsterdam, NL, vol. 39, May 6, 2016 pp. 25-33.
Yi Lu, et al; "Poly(3,4-ethylenedioxythiophene)/poly(styrenesulfonate)-poly(vinyl alcohol)/poly(acrylic acid) interpenetrating polymer networks for improving optrode-neural tissue interface in optogenetics" Biomaterials, Elsevier, Amsterdam NL, vol. 33, No. 2, Sep. 28, 2011, pp. 378-394.
Masato, Sasaki et al ;"Highly Conductive stretchable and biocompatible electrode-hydrogel hybrids for advanced tissue engineering" Advanced Healthcare materials, col. 3 No. 11, Jun. 10, 2014, pp. 1919-1927.
International Search Report for PCT/US20/31403, dated Nov. 16, 2021.
Annabi, N., Yue, K., Tamayol, A. & Khaderhosseini, A. Elastic sealants for surgical applications. European Journal of Pharmaceutics and Biopharmaceutics 95, 27-39 (2015).
Yuk, H., Lu, B. & Zhao, X. Hydrogel bioelectronics. Chemical Society Reviews, doi: 10.1039/C1038CS00595H (2018).
Karp, J. M. A Slick and Stretchable Surgical Adhesive. New England Journal of Medicine 377, 2092-2094 (2017)).
Li, J. et al. Tough adhesives for diverse wet surfaces. Science 357, 378-381 (2017)).
Ouyang, L. et al. Enhanced PEDOT adhesion on solid substrates with electrografted P (EDOT-NH2). Science Advances 3, e1600448 (2017)).
Yuk, H., Zhang, T., Lin, S., Parada, G. A. & Zhao, X. Tough bonding of hydrogels to diverse non-porous surfaces. Nature Materials 15, 190 (2016).
Yuk, H., Zhang, T., Parada, G. A., Liu, X. & Zhao, X. Skin-inspired hydrogel-elastomer hybrids with robust interfaces and functional microstructures. Nature Communications 7, 12028 (2016).
Wirthl, D. et al. Instant tough bonding of hydrogels for soft machines and electronics. Science Advances 3, e1700053 (2017)).
Rose, S. et al. Nanoparticle solutions as adhesives for gels and biological tissues. Nature 505, 382-385 (2014).
Boehler, C., Oberueber, F., Schlabach, S., Stieglitz, T. & Asplund, M. Long-term stable adhesion for conducting polymers in biomedical applications: IrOx and nanostructured platinum solve the chronic challenge. ACS Applied Materials & Interfaces 9, 189-197 (2016).
Boutry, C. M. et al. A stretchable and biodegradable strain and pressure sensor for orthopaedic application. Nature Electronics 1, 314-321 (2018).
Sadekar, A. G. et al. Robust PEDOT films by covalent bonding to substrates using in tandem sol-gel, surface initiated free-radical and redox polymerization. Journal of Materials Chemistry 22, 100-108 (2012).

(Continued)

*Primary Examiner* — Patrick D Niland
(74) *Attorney, Agent, or Firm* — Nieves IP Law Group, LLC; Peter A. Nieves

(57) ABSTRACT

Adhesion of conducting polymers on diverse insulating and conductive substrates via a hydrophilic adhesion layer, where one or more functional groups may be disposed between the substrate and the hydrophilic adhesion layer. Adhesion of the conducting polymers on the substrates is such that adhesion is maintained or substantially maintained in wet physiological environments.

31 Claims, 16 Drawing Sheets

(56) References Cited

OTHER PUBLICATIONS

Yuk, H. & Zhao, X. A new 3d printing strategy by harnessing deformation, instability, and fracture of viscoelastic inks. Advanced Materials 30, 1704028 (2018)).

Lu, B. et al. Pure PEDOT:PSS hydrogel with extraordinary electrical, mechanical and swelling properties. under review (2018).

Venkatraman, S. et al. In vitro and in vivo evaluation of PEDOT microelectrodes for neural stimulation and recording. IEEE Transactions on Neural Systems Rehabilitation Engineering 19, 307-316 (2011).

Roche, E. T. et al. Soft robotic sleeve supports heart function. Science Translational Medicine 9, eaaf3925 (2017).

Darnell, M. C. et al. Performance and biocompatibility of extremely tough alginate/polyacrylamide hydrogels. Biomaterials 34, 8042-8048 (2013)).

Vakalopoulos, K. A. et al. Mechanical strength and rheological properties of tissue adhesives with regard to colorectal anastomosis: an ex vivo study. Annals of Surgery 261, 323-331 (2015).

Cui, X. T. & Zhou, D. D. Poly (3, 4-ethylenedioxythiophene) for chronic neural stimulation. IEEE Transactions on Neural Systems Rehabilitation Engineering 15, 502-508 (2007).

Green, R. A. et al. Substrate dependent stability of conducting polymer coatings on medical electrodes. Biomaterials 33, 5875-5886 (2012).

Lee, B. P., Messersmith, P. B., Israelachvili, J. N. & Waite, J. H. Mussel-inspired adhesives and coatings. Annual Review of Materials Research 41, 99-132 (2011)).

Yamagishi, K. et al. Tissue-adhesive wirelessly powered optoelectronic device for metronomic photodynamic cancer therapy, Nature Biomedical Engineering 3, 27-36 (2019)).

Reece, T. B., Maxey, T. S. & Kron, I. L. A prospectus on tissue adhesives. The American Journal of Surgery 182, S40-S44 (2001)).

\* cited by examiner

STRONG ADHESION OF CONDUCTING POLYMERS ON DIVERSE SUBSTRATES

CROSS-REFERENCE TO RELATED APPLICATION

This application claims the benefit of U.S. Provisional Application No. 62/853,785, filed on May 29, 2019. The entire teaching of the above application is incorporated herein by reference.

GOVERNMENT SUPPORT STATEMENT

This invention was made with Government support under Grant No. CMMI-1661627 awarded by National Science Foundation (NSF). The Government has certain rights in the invention.

FIELD OF THE INVENTION

The present invention generally relates to materials and methods which provide strong adhesion of conducting polymers on a variety of insulating and conducting substrates, more particularly, to such materials and methods that provide and maintain strong adhesion even when exposed to moisture.

BACKGROUND OF THE INVENTION

Conducting polymers, such as poly(3,4-ethylenedioxythiophene):poly(styrene sulfonate) (PEDOT:PSS), polypyrrole (PPy), and polyaniline (PAni), have attracted great attention as promising bioelectronic interfaces with biological tissues owing to their favorable electrical and mechanical properties, electrochemical stability, and biocompatibility. However, the weak and unstable adhesion of conducting polymers to substrates, particularly in wet physiological environments, has greatly hindered their reliability and utility (e.g., see Cui, X. T. & Zhou, D. D. Poly (3, 4-ethylenedioxythiophene) for chronic neural stimulation. *IEEE Transactions on Neural Systems Rehabilitation Engineering* 15, 502-508 (2007); Green, R. A. et al. Substrate dependent stability of conducting polymer coatings on medical electrodes. *Biomaterials* 33, 5875-5886 (2012); Yuk, H., Lu, B. & Zhao, X. Hydrogel bioelectronics. *Chemical Society Reviews*, doi: 10.1039/C1038CS00595H (2018); Ouyang, L. et al. Enhanced PEDOT adhesion on solid substrates with electrografted P (EDOT-NH2). *Science Advances* 3, e1600448 (2017)). Such poor adhesion has been shown to result in interfacial failures (e.g., debonding of the conducting polymer) and the subsequent loss of optimal functionality, significantly damaging the long-term reliability and efficacy of bioelectronic devices fabricated using such materials (see Yuk, H., Zhang, T., Lin, S., Parada, G. A. & Zhao, X. Tough bonding of hydrogels to diverse non-porous surfaces. *Nature Materials* 15, 190 (2016); Yuk, H., Zhang, T., Parada, G. A., Liu, X. & Zhao, X. Skin-inspired hydrogel—elastomer hybrids with robust interfaces and functional microstructures. *Nature Communications* 7, 12028 (2016); Wirthl, D. et al. Instant tough bonding of hydrogels for soft machines and electronics. *Science Advances* 3, e1700053 (2017)).

In an effort to address these deficiencies, methods have been developed to provide enhanced adhesion of conducting polymers in wet environments. According to one method, topological modifications are made to a substrate in order to improve adhesion of conducting polymers on the substrate surface. For example, methods of modifying gold substrates with nano- and micro-scale roughness have been used (see Boehler, C., Oberueber, F., Schlabach, S., Stieglitz, T. & Asplund, M. Long-term stable adhesion for conducting polymers in biomedical applications: IrOx and nanostructured platinum solve the chronic challenge. *ACS Applied Materials & Interfaces* 9, 189-197 (2016); Pranti, A. S., Schander, A., Bödecker, A. & Lang, W. in *Multidisciplinary Digital Publishing Institute Proceedings.* 492). According to another method, chemically-modified 3,4-ethylenedioxythiophene (EDOT) monomers (e.g., vinyl-, carboxylic-, and amine-modified EDOT) are electro-deposited onto a substrate to improve adhesion of PEDOT:PSS to the substrate (see Ouyang, L. et al. Enhanced PEDOT adhesion on solid substrates with electrografted P (EDOT-NH2). *Science Advances* 3, e1600448 (2017); Sadekar, A. G. et al. Robust PEDOT films by covalent bonding to substrates using in tandem sol-gel, surface initiated free-radical and redox polymerization. *Journal of Materials Chemistry* 22, 100-108 (2012); Wei, B., Liu, J., Ouyang, L., Kuo, C.-C. & Martin, D. C. Significant enhancement of PEDOT thin film adhesion to inorganic solid substrates with EDOT-acid. *ACS Applied Materials & Interfaces* 7, 15388-15394 (2015)).

While currently available methods provide some improvements in adhesion, they require either complicated modification of the EDOT monomer and/or are only usable with specific types of substrates, and they are limited to electro-deposited PEDOT:PSS on conductive substrates. As such, current methods substantially limit the applicability and utility of conductive polymers, particularly in wet environments. Thus, further improvements are greatly needed.

SUMMARY OF THE INVENTION

According to one aspect, the present invention provides a device for use in a wet environment comprising: a substrate material fabricated of an insulating or conducting material, or a combination thereof, the substrate material having a top surface and a bottom surface; a hydrophilic adhesion layer disposed on at least a portion of one or more of the top surface and bottom surface; and one or more conducting polymers adhered to at least a portion of one or more of the top surface and bottom surface of the substrate material via the hydrophilic adhesion layer, wherein the one or more conducting polymers are adhered with an adhesion strength that is substantially maintained when the implantable device is exposed to the wet environment.

Embodiments according to this aspect can include one or more of the following features. The hydrophilic adhesion layer can be fabricated of at least one hydrophilic elastomer. The at least one hydrophilic elastomer can be chosen from at least one polyvinyl alcohol (PVA), hydrophilic polyurethane, hydrophilic epoxy, hydrophilic silicone, latex, polyacrylamide, polyethylene glycol, polyhydroxy ethyl methacrylate, polyhydroxy ethyl acrylate, poly acrylic acid, copolymers thereof, and combinations thereof. According to an embodiment, the hydrophilic elastomer is a hydrophilic polyurethane. The hydrophilic adhesion layer can be a hydrophilic polyurethane adhesion layer. The device can further comprise functional groups disposed between the substrate material and the hydrophilic adhesion layer. The functional groups can be selected from primary amine groups, carboxylic acid groups, thiol groups, vinyl groups, epoxide groups, succinimide groups, hydroxy groups, and combinations thereof. The adhesion layer can be a polyurethane adhesion layer and the functional groups can be primary amine groups. The substrate can be fabricated of materials selected from glass, silicon, polyimide, polycarbonate, perylene, polypropylene, polymethyl methacrylate (PMMA), polyethylene terephthalate (PETE), polydimethylsiloxane (PDMS), polyurethane, styrene-ethylene-butylene-styrene (SEBS), indium tin oxide (ITO), gold, platinum, titanium, titanium nitride, iridium, iridium oxide and combinations thereof. The substrate can be a multielectrode array. The conducting polymers can be selected from poly (3,4-ethylenedioxythiophene) (PEDOT), poly(3,4-ethylenedioxythiophene) polystyrene sulfonate (PEDOT:PSS), polythiophene, poly(p-phenylene sulfide), polypyrrole (PPy), polycarbazole, polyindole, polyazepine, polyaniline (PAni) and combinations thereof. The device can further comprise an interpenetrating layer formed on exposure of the device to the wet environment, the interpenetrating layer disposed between the conducting polymer and the hydrophilic adhesion layer. The interpenetrating layer can be formed of interpenetrating networks between the conducting polymer and the hydrophilic adhesion layer. The device can be a wearable or implantable device. The device can be an implantable bioelectronic device.

According to another aspect, the present invention provides a method for forming a device, which is disposed within or in contact with bodily fluids or which is used in a wet environment, comprising: obtaining a substrate, the substrate having a top surface and a bottom surface; disposing a hydrophilic adhesion layer on at least a portion of one or more of the top surface and bottom surface of the substrate; and adhering one or more conducting polymers to at least a portion of one or more of the top surface and bottom surface of the substrate via the hydrophilic adhesion layer, wherein the one or more conducting polymers are adhered with an adhesion strength that is substantially maintained when the implantable device is exposed to the wet environment.

Embodiments according to this aspect can include one or more of the following features. The hydrophilic adhesion layer can be fabricated of at least one hydrophilic elastomer. The at least one hydrophilic elastomer can be chosen from at least one polyvinyl alcohol (PVA), hydrophilic polyurethane, hydrophilic epoxy, hydrophilic silicone, latex, polyacrylate, polyacrylamide, polyethylene glycol, polyhydroxy ethyl methacrylate, polyhydroxy ethyl acrylate, poly acrylic acid, copolymers thereof, and combinations thereof. According to an embodiment, the hydrophilic elastomer is a hydrophilic elastomer. The hydrophilic adhesion layer can be a hydrophilic polyurethane adhesion layer. The method can further comprise prior to disposing the hydrophilic adhesion layer, functionalizing the substrate with one or more functional groups selected from primary amine groups, carboxylic acid groups, thiol groups, vinyl groups, epoxide groups, succinimide groups, hydroxy groups, and combinations thereof. The adhesion layer can be a polyurethane adhesion layer and the functional groups can be primary amine groups. The substrate can be fabricated of insulating materials, conducting materials, or combinations thereof. The substrate can be fabricated of materials selected from glass, silicon, polyimide, polycarbonate, perylene, polypropylene, polymethyl methacrylate (PMMA), polyethylene terephthalate (PETE), polydimethylsiloxane (PDMS), polyurethane, styrene-ethylene-butylene-styrene (SEBS), indium tin oxide (ITO), gold, platinum, titanium, titanium nitride, iridium, iridium oxide and combinations thereof. The substrate can be a multielectrode array. The conducting polymers can be selected from poly(3,4-ethylenedioxythiophene) (PEDOT), poly(3,4-ethylenedioxythiophene) polystyrene sulfonate (PEDOT:PSS), polythiophene, poly(p-phenylene sulfide), polypyrrole (PPy), polycarbazole, polyindole, polyazepine, polyaniline (PAni) and combinations thereof. The conducting polymers can be adhered by solvent-casting or electro-deposition methods. The hydrophilic adhesion layer can be disposed on the substrate material by spin-coating, spray-coating, dip-coating, or combinations thereof. The step of adhering one or more conducting polymers can comprises using a precursor solution containing moisture to trigger swelling of the hydrophilic adhesion layer, and the method further comprises, allowing the hydrophilic adhesion layer to swell, and allowing the conducting polymer to diffuse into and through the hydrophilic adhesion layer to form an interpenetrating layer. The interpenetrating layer can be formed between the conducting polymer and the hydrophilic adhesion layer. The interpenetrating layer can be formed by interpenetrating networks between the conducting polymer and the hydrophilic adhesion layer. The interpenetrating layer can be a bridging interface providing increased interfacial adhesion between the conducting polymer and the hydrophilic adhesion layer coated substrate in the wet environment.

Other systems, methods and features of the present invention will be or become apparent to one having ordinary skill in the art upon examining the following drawings and detailed description. It is intended that all such additional systems, methods, and features be included in this description, be within the scope of the present invention and protected by the accompanying claims.

BRIEF DESCRIPTION OF THE DRAWINGS

The accompanying drawings are included to provide a further understanding of the invention, and are incorporated in and constitute a part of this specification. The components in the drawings are not necessarily to scale, emphasis instead being placed upon clearly illustrating the principles of the present invention. The drawings illustrate embodiments of the invention and, together with the description, serve to explain the principals of the invention.

FIG. 1B illustrating adhesion of a conducting polymer on a substrates with a polyurethane adhesion layer in a wet environment, according to an embodiment of the present invention; FIG. 1C illustrating adhesion of a conducting polymer on a pristine substrate without a polyurethane adhesion layer in a wet environment; FIG. 1D illustrating mechanical deformations of solvent-casted wet PEDOT:PSS on a polyimide substrate with a PU-adhesion layer, according to an embodiment of the present invention; FIG. 1E illustrating mechanical deformation of a solvent-casted wet PEDOT:PSS on a pristine polyimide substrate; FIG. 1F showing the distribution of carbon and sulfur atoms in an adhesion interface between PEDOT:PSS and a PU-coated silicon substrate, according to an embodiment of the present invention.

FIG. 2B illustrating platinum, FIG. 2C illustrating gold, and FIG. 2D illustrating polyimide.

DETAILED DESCRIPTION

Figure 1:
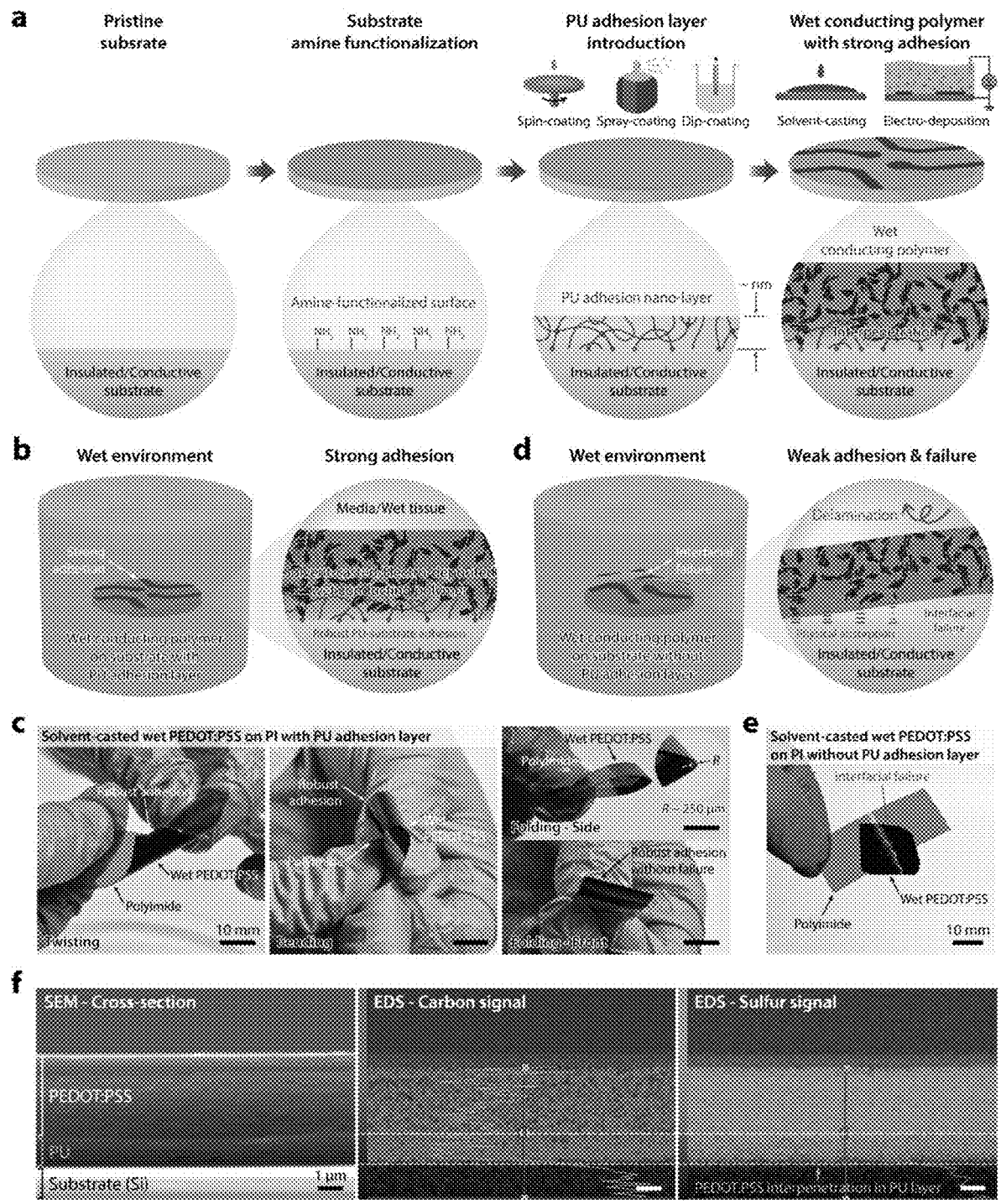
FIGS. 1A-F schematically illustrate the adhesion of conducting polymers on a variety of substrate materials, with FIG. 1A showing a process for adhering conducting polymers on polyurethane-coated (PU-coated) amine-functionalized substrates, according to an embodiment of the present invention.
Figure 2:
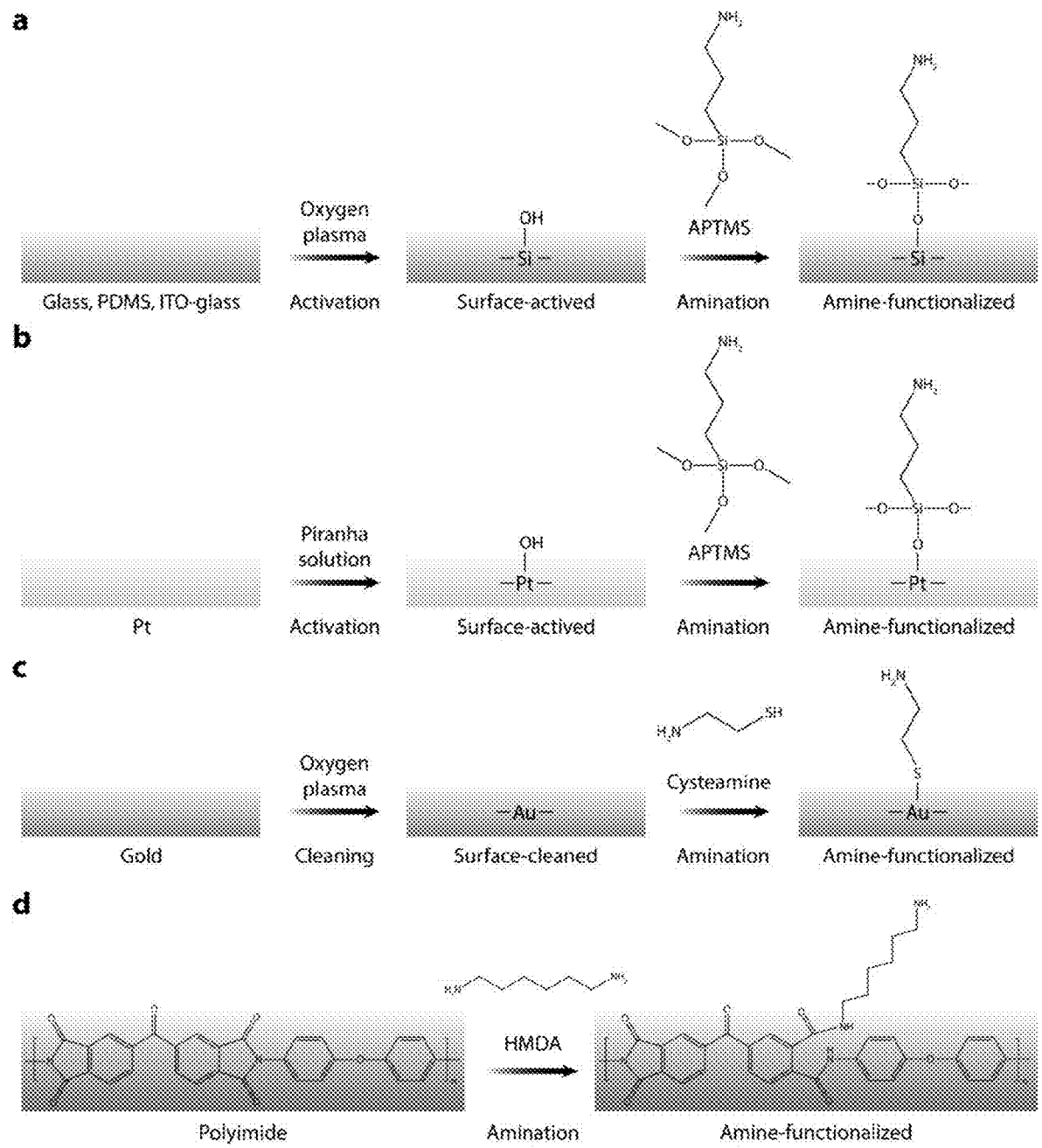
FIGS. 2A-D schematically illustration primary amine functionalization of a variety of substrates, according to embodiments of the present invention, with FIG. 2A illustrating glass, polydimethylsiloxane (PDMS), indium-tin-oxide (ITO) coated glass.

The following definitions are useful for interpreting terms applied to features of the embodiments disclosed herein, and are meant only to define elements within the disclosure.

As used herein, the term "maintain adhesion", "substantially maintain adhesion", "not decrease adhesion" or "not significantly decrease adhesion", when used to describe the strength of adhesion of the conducting polymers on the substrates before and after exposure to a wet physiological environment, refers to a maximum decrease in adhesion strength of no greater than 10%. The decrease in adhesion strength is a decrease from an initial adhesion strength as measured prior to exposure to a wet physiological environment, to a wet adhesion strength as measured after exposure to a wet physiological environment. The time of measurement after exposure to a wet physiological environment is not particularly limited but is generally measured at least 1 minute after exposure and up to 3 months.

As used herein a "wet environment", "moisture", and "wet physiological environment", when used to describe that adhesion strength is maintained even upon exposure to a "wet environment", "moisture", and "wet physiological environment", refers to a moisture content from water, saline, moisture, and physiological body fluids such as blood plasma, interstitial fluid, lymphatic fluid, cerebrospinal fluid, and gastrointestinal fluid. For example, such a "wet environment", "moisture", and "wet physiological environment" would be encountered when the device is used as a wearable and implantable bioelectronic device in contact or within biological systems, a device installed in humid environment, and a device installed in an underwater environment.

As used herein "strong adhesion" refers to an adhesion which exhibits a lap-shear strength of at least about 100 kPa, and which exhibit no observable interfacial failure (i.e., observable interfacial failure, wherein interfacial failure is as defined below and would include any degree of interfacial delamination) at least after 1 min of ultrasonication, 1,000 charging and discharging cycles, or 1,000 bending cycles.

As used herein "stable adhesion" refers to an adhesion which sustains the adhesion between the conducting polymer and the device substrate without interfacial failure during the device's ordinary operation and usage.

As used herein, "interfacial failure" refers to any degree of interfacial delamination, which would range all the way from complete delamination of the entire interfacial adhesion to partial delamination of any portion of the interfacial adhesion that are observable in macroscale by the naked eye or in microscale by microscopic imaging under a maximum magnification of 20×.

As used herein, an "insulating material" or "insulating substrate" refers to materials lacking of transmitting electrical currents typically with the electrical conductivity lower than $10^{-9}$ S/m at room temperature.

As used herein, a "conducting material", "conductive material", "conducting substrate" and "conductive substrate" refers to materials with the capability to transmit electrical currents typically with the electrical conductivity higher than $10^{-3}$ S/m at room temperature.

As used herein, a "conducting polymer" and "conductive polymer" refers to electrically conductive polymers that are capable of transmitting electrical currents typically with the electrical conductivity higher than $10^{-3}$ S/m at room temperature.

As used herein, "mechanically stable" refers to the quality of interfacial adhesion that can withstand mechanical stimuli such as deformation without interfacial failure.

As used herein, "electrochemically stable" refers to the quality of interfacial adhesion that can withstand electrochemical stimuli such as charging and discharging of electrical currents without interfacial failure.

The present invention generally provides a method to achieve strong adhesion of various conducting polymers on diverse insulating and conductive substrates, particularly wherein such adhesion is maintained or substantially maintained in wet physiological environments. The present invention further provides devices which include an insulating or conductive substrate with one or more conducting polymers adhered to at least a portion of one or more surfaces of the substrate. Such conducting polymers are adhered to the substrate in such a way that exposure of the device to a wet physiological environment does not decrease or significantly decrease adhesion between the conducting polymers and substrate.

In particular, the present invention provides a hydrophilic adhesion layer disposed on at least a portion of the substrate surface to which the conducting polymer is to be adhered. The adhesion layer may be any hydrophilic elastomer adhesion layer, and according to embodiments of the present invention, suitable hydrophilic elastomers include, but are not limited to, polyvinyl alcohol (PVA), hydrophilic polyurethane, hydrophilic epoxy, hydrophilic silicone, latex, polyacrylamide, polyethylene glycol, polyhydroxy ethyl methacrylate, polyhydroxy ethyl acrylate, poly acrylic acid, their copolymers, and combinations thereof. According to an embodiment of the invention, the adhesion layer is a hydrophilic polyurethane (PU) adhesion layer. The hydrophilic adhesion layer serves as a bridging layer between the substrate surface and the conductive polymer. This hydrophilic adhesion layer is generally applied at nanoscale thickness (i.e., a thickness ranging from about 1 to about 100 nm) and can be effectively applied to any substrate surface regardless of whether the surface is smooth or has some texture or roughness. The hydrophilic adhesion layer can be easily introduced on a broad range of substrate materials via any conventional fabrication approaches, including but not limited to, spin-coating, spray-coating, and dip-coating.

After the hydrophilic adhesion layer is disposed on the desired substrate surface, one or more conducting polymers are introduced to provide a unique interpenetration of conducting polymer through the hydrophilic adhesion layer (as later described in more detail, this "unique interpenetration" is depicted in FIG. 1A where the diffusion of the conducting polymer precursor forms an interpenetrating layer through the hydrophilic adhesion layer, where the hydrophilicity and subsequent swelling of the hydrophilic adhesion layer in a wet environment allows for the diffusion of conducting polymer precursor into and through the hydrophilic adhesion layer during the formation of conducting polymer) the resultant interfacial adhesion of the conducting polymers is strong and mechanically and electrochemically stable. In particular, devices of the present invention exhibit lap-shear strength over 120 kPa, and exhibit no observable interfacial failure after 60 min of ultrasonication and 10,000 charging and discharging cycles.

As such, unlike currently available techniques which require the use of complex chemical syntheses and/or substrate modifications, the present invention allows for the use of commercially available materials, such as conducting polymers and hydrophilic polyurethanes. The present invention thus enables ready and broad dissemination for existing and new bioelectronic devices. Furthermore, the present method is compatible with various fabrication approaches for conducting polymers, including solvent-casting and electro-deposition, without compromising the mechanical and electrical properties of the materials. Further, the present invention provides outstanding adhesion strength, conductivity, and mechanical and electrochemical stability on various insulating and conductive substrates, as well as commercially-available multielectrode arrays. As such, not only does the present invention address the challenges of robust integration of conducting polymers in bioelectronic devices, but it also a provides a method for achieving strong adhesion between various hydrogels and substrates.

According to the present invention, a wide variety of conventional insulating and conductive substrates may be utilized. For example, conventional insulating and conductive substrates used in bioelectronic devices, such as glass, silicon, polyimide, polycarbonate, perylene, polypropylene, polymethyl methacrylate (PMMA), polyethylene terephthalate (PETE), polydimethylsiloxane (PDMS), polyurethane, styrene-ethylene-butylene-styrene (SEBS), indium tin oxide (ITO), gold, platinum, titanium, titanium nitride, iridium, iridium oxide, and combinations thereof may be suitably used as the substrate material in the present invention. The present invention further allows for the strong adhesion of conducting polymers to commercially available multielectrode arrays. Thus, the present materials and methods can be used to provide wearable and implantable bioelectronic devices. When used as a wearable or implantable bioelectronic device, the substrate material, as well as all other components of the device, are suitably biocompatible materials.

According to the present invention, a wide range of commercially available conducting polymers can be strongly adhered to the various substrate materials. Suitable conducting polymers include, but are not limited to poly(3,4-ethylenedioxythiophene) (PEDOT), poly(3,4-ethylenedioxythiophene) polystyrene sulfonate (PEDOT:PSS), polythiophene, poly(p-phenylene sulfide), polypyrrole (PPy), polycarbazole, polyindole, polyazepine, polyaniline (PAni), and combinations thereof.

Reference will now be made in detail to embodiments of the present invention, examples of which are illustrated in the accompanying drawings. Wherever possible, the same reference numbers are used in the drawings and the description to refer to the same or like parts.

According to an embodiment of the present invention, a method for adhering one or more conducting polymers onto a diverse range of substrates is illustrated in FIG. 1A. A pristine substrate is functionalized by functional groups that enhance adhesion of the hydrophilic adhesion layer (which can be any hydrophilic adhesion layer, but may hereinafter be specifically referred to as a polyurethane adhesion layer, PU adhesion layer, or PU layer for simplicity sake, but which is not intended to limit the present invention only to use of a polyurethane adhesion layer) to the substrate. According to preferred embodiments, the functional groups may be selected from primary amine groups, carboxylic acid groups, thiol groups, vinyl groups, epoxide groups, succinimide groups, hydroxy groups, and combinations thereof. These functional groups may suitably vary depending upon the adhesion layer material used in a given case. For example, when the adhesion layer is fabricated of polyurethane (PU), latex, and/or polyacrylic acid, primary amine groups are particularly suitable for use as the functional groups. When the adhesion layer is fabricated of polyvinyl alcohol (PVA), polyethylene glycol, polyhydroxy ethyl methacrylate, and polyhydroxy ethyl acrylate, hydroxy groups are particularly suitable for use as the functional groups. When the adhesion layer is fabricated of epoxy, epoxide groups are particularly suitable for use as the functional groups. When the adhesion layer is fabricated of silicone, vinyl groups are particularly suitable for use as the functional groups. When the adhesion layer is fabricated of polyacrylamide, succinimide and carboxylic acid groups are particularly suitable for use as the functional groups. Further, when the adhesion layer is fabricated of a combination of one or more of materials, the functional groups can include one or more of the above-noted materials and may be suitably determined by one skilled in the art.

Surface functionalization of the substrate surface can be carried out using any conventional functionalization method. According to an embodiment of the present invention, a solution containing a suitable amine group, which is generally selected depending upon the substrate material, is prepared, followed by immersion of the substrate in the solution for a suitable time (e.g., typically about 30 min) or the functionalization reaction to occur. Functionalization of the substrate surface has been determined to provide enhanced interfacial adhesion between the substrate and a subsequent hydrophilic elastomer adhesion layer, such as one or more of those listed above, and in an exemplary embodiment a hydrophilic polyurethane (PU), via electrostatic or covalent interactions.

After the substrate surface has been functionalized, a hydrophilic adhesion layer (e.g., PU) is applied. The hydrophilic adhesion layer can be applied to a wide range of substrate materials and geometries using various coating approaches including, for example, spin-coating, spray-coating, and dip-coating. As such, methods of the present invention can advantageously utilize the high processability of commercially available hydrophilic polyurethane, hydrophilic polyvinyl alcohol (PVA), hydrophilic epoxy, hydrophilic silicone, latex, polyacrylamide, polyethylene glycol, polyhydroxy ethyl methacrylate, polyhydroxy ethyl acrylate, poly acrylic acid, their copolymers, and combinations thereof.

After the hydrophilic adhesion layer is deposited on the substrate, conducting polymers are then disposed on the adhesion layer coated substrate using a variety of approaches such as, but not limited to, solvent-casting of an aqueous solution of the conducting polymers, or electro-deposition of suitable monomer precursors. As previously noted, the conducting polymers may be selected from one or more of those listed above, namely poly(3,4-ethylenedioxythiophene) (PEDOT), poly(3,4-ethylenedioxythiophene) polystyrene sulfonate (PEDOT:PSS), polythiophene, poly(p-phenylene sulfide), polypyrrole (PPy), polycarbazole, polyindole, polyazepine, and polyaniline (PAni), or any other conventional conducting polymer. Such conducting polymers can be prepared by either solvent-casting or electro-deposition on the hydrophilic adhesion layer coated substrates.

For example, PEDOT:PSS can be prepared on a PU adhesion layer coated substrates via solvent-casting the aqueous PEDOT:PSS dispersion with 15 v/v % dimethyl sulfoxide (DMSO) followed by followed by air-drying for 12 h at room temperature and subsequent annealing for 30 min at 120° C. Alternatively, PEDOT:PSS can also be prepared on the PU adhesion layer coated substrate via electro-deposition of 3,4,-ethylenedioxythiophene styrene sulfonate (EDOT:PSS) precursor solution with by an electropolymerization under applied potential across the precursor solution and the substrate.

PPy can be prepared on the PU adhesion layer coated substrates via solvent-casting aqueous pyrrole precursor solution mixed with the aqueous oxidant solution (such as ammonium persulfate) as a polymerization reagent. PAni can be prepared on the PU adhesion layer coated substrates via solvent-casting aqueous aniline precursor solution mixed with the aqueous oxidant solution (such as ammonium persulfate) as a polymerization reagent.

During the formation of conducting polymers, the diffusion of the conducting polymer precursor forms an interpenetrating layer through the hydrophilic adhesion layer, as depicted in FIG. 1A. In particular, as shown in FIG. 1A, the hydrophilicity and subsequent swelling of the hydrophilic PU adhesion layer in a wet environment allows for the diffusion of conducting polymer precursor into and through the PU adhesion layer during the formation of conducting polymer by solvent-casting or electro-deposition. In particular, formation of the interpenetrating layer occurs during the formation of the conducting polymer (e.g. by solvent-casting of a precursor solution or electro-deposition), wherein a precursor solution used to prepare the conducting polymer provides the moisture which triggers and generates interpenetration through the hydrophilic adhesion layer.

The high compatibility of the hydrophilic adhesion layer with the conducting polymers enables the formation of interpenetrating networks between the infiltrated conducting polymer and the adhesion layer during deposition of the conducting polymers (e.g., via a solvent-casting or electro-deposition process) on the adhesion layer coated substrate.

Figure 3:
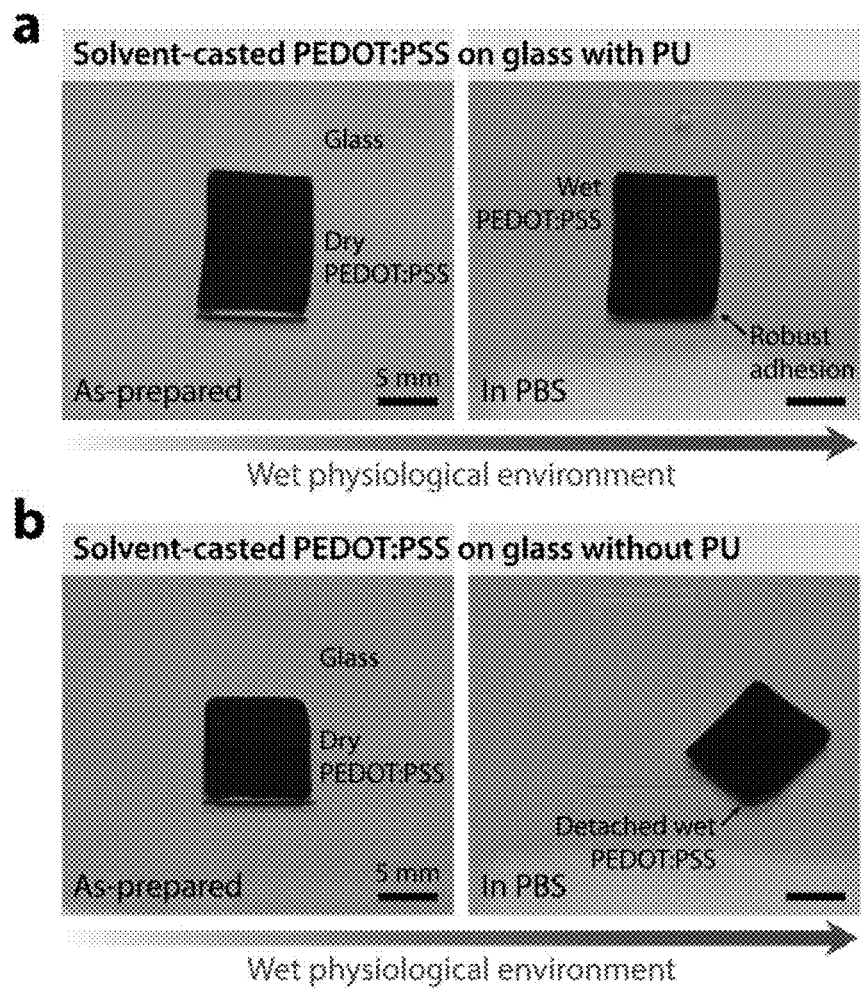
FIGS. 3A-B showing images of solvent-casted PEDOT:PSS on glass substrates with a PU-adhesion layer as prepared and in a wet physiological environment, according to an embodiment of the present invention (FIG. 3A), and without a PU-adhesion layer as prepared and in a wet physiological environment (FIG. 3B).

This resultant interpenetrating layer acts as bridging interface between the conducting polymer and the adhesion layer coated substrate in wet physiological environments, providing strong interfacial adhesion. This was demonstrated by providing pristine substrates (i.e., no polyurethane adhesion layer disposed thereon) (e.g., see FIGS. 1C and 1E), and adhering a conducting polymer to the pristine substrate. In particular, adhesion between conducting polymers and pristine substrates is typically maintained by physical absorption of the conducting polymers onto the pristine substrate surface, which is weak and cannot provide robust adhesion in a wet environment (FIG. 1C). On the other hand, adhesion between conducting polymers and a substrate having a hydrophilic adhesion layer deposited thereon in accordance with the present invention provides strong adhesion in a wet environment (FIG. 1B). As depicted in FIG. 1E, the solvent-casted wet PEDOT:PSS on the pristine polyimide without a hydrophilic adhesion layer easily undergoes interfacial failure upon mechanical deformation of the polyimide substrate. On the other hand, the solvent-casted wet PEDOT:PSS on the insulating and flexible substrate (i.e., polyimide) with a deposited PU adhesion layer exhibited robust adhesion without failure under twisting, bending, and even folding (with the radius of curvature ~250 μm)(FIG. 1D). As further illustrated in FIG. 3A, a solvent casted PEDOT:PSS on a glass substrate having a PU adhesion layer thereon exhibited robust adhesion with no delamination upon swelling in PBS (FIG. 3A). In contrast, as illustrated in FIG. 3B, a solvent casted PEDOT:PSS on a pristine glass substrate without a deposited hydrophilic adhesion layer exhibits a spontaneous delamination failure upon swelling in PBS.

Figure 4:
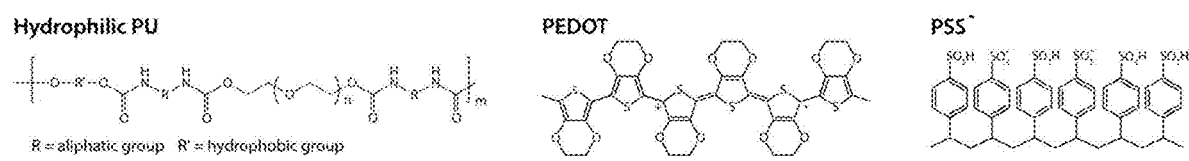
FIG. 4 illustrates the chemical structures of hydrophilic polyurethane, PEDOT, and PSS.

To validate the formation of an interpenetrating layer between the conducting polymer and the PU adhesion layer, the elemental dispersion of carbon and sulfur atoms were examined in cross-section of a cryo-fractured sample (the solvent-casted PEDOT:PSS on PU-coated Si wafer) by SEM-EDS (Scanning Electron Microscopy/Energy Dispersive X-Ray Spectroscopy) (FIG. 1F). Since both PEDOT and PSS contain sulfur, while hydrophilic PU is absent of sulfur (as shown in FIG. 4), the sulfur signal can serve as an indicator for the interpenetration of PEDOT:PSS into the PU adhesion layer. In FIG. 1F (right photo), it is evident that the sulfur signal is detected in the PU adhesion layer, clearly indicating the interpenetration of the PEDOT:PSS through the hydrophilic PU adhesion layer. Further, PEDOT:PSS was shown to interpenetrate through the PU adhesion layer through optical microscopy (see FIG. 5). In particular, looking to FIG. 5, the cross-section image of the wet PEDOT:PSS layer (thickness, 21±1.2 μm) on the thick PU adhesion layer (thickness, 1 mm) shows a further layer, which is the interpenetrating layer (thickness, 51.4±1.5 μm) extending toward the PU adhesion layer.

Thus, the present invention, wherein an interpenetrating layer is formed between the conducting polymer and the hydrophilic adhesion layer, provides a mechanically robust anchorage against interfacial failures, particularly in wet environments.

The following non-limiting examples are illustrative of the invention, and were conducted in accordance with the following Materials and Methods parameters.

Materials and Methods

Primary Amine Functionalization of Diverse Substrates

To functionalize glass, PDMS, and ITO-glass with primary amine groups, the substrates were first cleaned by washing with acetone, ethanol, and deionized in order followed by drying under nitrogen flow. The cleaned substrates were then activated by oxygen plasma (30 W at 20 mTorr pressure, Harrick Plasma) for 3 min (1 min for PDMS). After oxygen plasma treatment, the substrates were immersed in 50 mL of silane solution (10 μL acetic acid, 1 w/v % 3-aminopropyl trimehtoxysilane (APTMS; TCI) in 100 mL deionized water) for 1 hour at room temperature. After incubation in the silane solution, the substrates were thoroughly washed with deionized water and dried under nitrogen flow.

To functionalize the platinum electrode with primary amine groups, the substrates were first cleaned by Piranha solution (3:1 mixture of concentrated sulfuric acid and 30% hydrogen peroxide solution). The cleaned substrates were then washed with deionized water and dried under nitrogen flow. The substrates were then immersed in 50 mL of silane solution (10 acetic acid, 1 w/v % 3-aminopropyl trimehtoxysilane in 100 mL deionized water) for 1 hour at room temperature. After incubation in the silane solution, the substrates were thoroughly washed with deionized water and dried under nitrogen flow.

To functionalize gold or MEA (with Au electrodes) with primary amine groups, the substrates were first cleaned by washing with acetone, ethanol, and deionized in order followed by drying under nitrogen flow. The cleaned substrates were then further cleaned by oxygen plasma (30 W at 20 mTorr pressure, Harrick Plasma) for 3 min. After oxygen plasma treatment, the substrates were immersed in 50 mL of 1 mM aqueous cysteamine solution for 1 hour at room temperature. After incubation in the cysteamine solution, the substrates were thoroughly washed with deionized water and dried under nitrogen flow.

To functionalize polyimide with primary amine groups, the substrates were first cleaned by washing with acetone, ethanol, and deionized in order followed by drying under nitrogen flow. The cleaned substrates were then immersed in 50 mL of 10 w/v % aqueous hexamethylenediamine (HMDA; Sigma-Aldrich) solution for 6 hours at room temperature. After incubation in the HMDA solution, the substrates were thoroughly washed with deionized water and dried under nitrogen flow.

Formation of Strong Adhesion of Conducting Polymers

A hydrophilic polyurethane (HydroMed D3, Advan-Source) was used as PU adhesion layers. To prepare a hydrophilic PU solution, varying concentrations of PU were dissolved in a 95:5 mixture of ethanol and deionized water. For planar substrates, the PU adhesion layer was introduced via spin-coating of the hydrophilic PU solution at 2000 rpm for 30 seconds. For substrates incompatible to spin-coating (such as non-planar substrates), the PU adhesion layer was introduced in controlled manner via dip-coating of the hydrophilic PU solution with pulling-rate of 1 cm $min^{-1}$. After spin-coating or dip-coating, the PU-coated substrates were baked at 80° C. for 10 min. For strong adhesion of wet conducting polymers, conducting polymers were prepared either by solvent-casting or electro-deposition on the PU-coated substrates following the previously reported protocols (e.g., see Ouyang, L. et al. Enhanced PEDOT adhesion on solid substrates with electrografted P(EDOT-NH2). *Science Advances* 3, e1600448 (2017); Lu, B. et al. Pure PEDOT:PSS hydrogel with extraordinary electrical, mechanical and swelling properties. under review (2018); Bo, J. et al. Morphology-controlled fabrication of polypyrrole hydrogel for solid-state supercapacitor. *Journal of Power Sources* 407, 105-111 (2018); Guo, H., He, W., Lu, Y. & Zhang, X. Self-crosslinked polyaniline hydrogel electrodes for electrochemical energy storage. *Carbon* 92, 133-141 (2015)).

For solvent-casted PEDOT:PSS, 15 v/v % dimethyl sulfoxide (DMSO; Sigma-Aldrich) was added into a commercially-available aqueous PEDOT:PSS dispersion (Clevious™ PH1000, Heraeus Electric Materials) and vigorously stirred for 6 hours at room temperature. The mixed PEDOT:PSS dispersion was then filtered by a PTFE filter (pore size, 5 µm) and solvent-casted on the PU-coated substrates followed by air-drying for 12 hours at room temperature and subsequent annealing for 30 min at 120° C. To obtain wet PEDOT:PSS adhered on the substrate, the samples were soaked in PBS for 1 hour before use.

For solvent-casted polypyrrole (PPy), an aqueous pyrrole solution (0.3 M pyrrole and 0.1 M sodium dodecyl sulfate in deionized water) and an aqueous oxidant solution (0.3 M ammonium persulfate in deionized water) were mixed in 1:1 volume ratio, and vigorously stirred for 3 min at room temperature. The mixed solution was solvent-casted on the PU-coated substrates and incubated in ambient conditions for 30 min. To obtain wet PPy adhered on the substrate, the samples were soaked in PBS for 1 hour before use.

For solvent-casted polyaniline (PAni), an aqueous aniline solution (1.42 M aniline and 1.42 M hydrochloric acid in deionized water) and an aqueous oxidant solution (1.42 M ammonium persulfate in deionized water) were mixed in 1:1 volume ratio, and vigorously stirred for 1 min at 4° C. The mixed solution was solvent-casted on the PU-coated substrates and incubated in ambient conditions for 30 min. To obtain wet PAni adhered on the substrate, the samples were soaked in PBS for 1 hour before use.

For electro-deposited PEDOT:PSS, PEDOT:PSS precursor solution (0.02 M 3,4,-ethylenedioxythiophene (EDOT; Sigma-Aldrich), 0.04 M PSS (Sigma-Aldrich), and 0.1 M $LiClO_4$ (Sigma-Aldrich) in deionized water was electro-deposited by an electrochemical potentiostat/galvanostat (PGSTAT30, Metrohm Autolab). The PU-coated electrodes, Pt sheets, and Ag/AgCl were used as a working electrode, a counter electrode, and a reference electrode, respectively. The electro-deposition was performed at 1.0 V vs. Ag/AgCl (38 mC $cm^{-2}$) for ITO-glass and at 1.0 V vs. Ag/AgCl (43 mC $cm^{-2}$) for MEA with Au electrodes.

Measurement of PU Adhesion Layer Thickness

The thicknesses of PU adhesion layers were measured by an ellipsometer (Gaertner Scientific) with a wavelength at 633 nm. The ellipsometer measured changes in polarization as a function of the sample thickness, which were then used to determine thickness of the PU adhesion layers.

Elemental Analysis of Adhesion Interfaces

The elemental distribution in the adhesion interfaces was characterized by SEM-EDS measurements of the cross-section of dry PEDOT:PSS on the PU-coated silicon substrate. The PEDOT:PSS on the PU-coated silicon substrate was immersed in liquid nitrogen for 3 min, and then cryo-fractured to obtain a clean cross-section. The cleaved sample was observed by SEM EDS (6010LA, JEOL) and characterized to monitor the distribution of carbon and sulfur atoms.

Mechanical Characterizations

Interfacial shear strength was measured by lap-shear tests with a prescribed overall area (length, 20 mm; width, 25 mm). The lap-shear test samples were prepared by solvent-casting of conducting polymers. A hydrophilic nylon filter (pore size, 1 µm, TISCH Scientific) was covered on top of a conducting polymer precursor solution on the substrate to provide a robustly integrated backing. Before the lap-shear tests, all samples were immersed in PBS for 1 hour to hydrate the conducting polymers. The lap-shear tests were performed by using a mechanical testing machine (2 kN load cell, Zwich/Roell Z2.5) at the crosshead speed of 50 mm $min^{-1}$. The interfacial shear strength was determined by dividing the peak measured force by the overlap area. Tensile tests were performed in a PBS bath with dog-bone shape samples by using a mechanical tester (U-stretch, CellScale) to avoid dehydration of wet PEDOT:PSS during the tests.

Electrical Characterizations

Electrical conductivity was measured by using a standard four-point probe (SCS-4200, Keithley) in deionized water. The electrical properties of the adhesion interfaces were characterized by measuring the sheet resistance ratio between the wet PEDOT:PSS and the ITO-glass electrodes by using a digital multimeter (Fluke). Electrochemical impedance spectroscopy (EIS) measurements were performed by using a potentiostat/galvanostat (1287A, Solartron Analytical) and a frequency response analyzer (1260A, Solatron Analytical) in an electrochemical cell installed with a platinum sheet as a counter electrode, Ag/AgCl as a reference electrode, and PBS as an electrolyte media. A frequency range between 0.1 and 100 kHz was scanned with an applied bias of 0.01 V vs. Ag/AgCl.

Cyclic voltammetry (CV) measurements were performed by using the electrochemical potentiostat/galvanostat (PGSTAT30, Metrohm Autolab) in an electrochemical cell installed with a platinum sheet as both working electrodes, Ag/AgCl wire as a reference electrode, and PBS as an electrolyte media. The charge storage capability (CSC) of the sample was calculated from the measured CV data as $$CSC = \int_{E_2}^{E_1} \frac{i(E)}{2vA} dE$$

where v is the scan rate, E2 and E1 are the potential window, i is the current at each potential, and A is the area of the wet PEDOT:PSS on the platinum electrode.

Example 1: Strong Adhesion of Wet Conducting Polymers on Diverse Substrates

Figure 6:
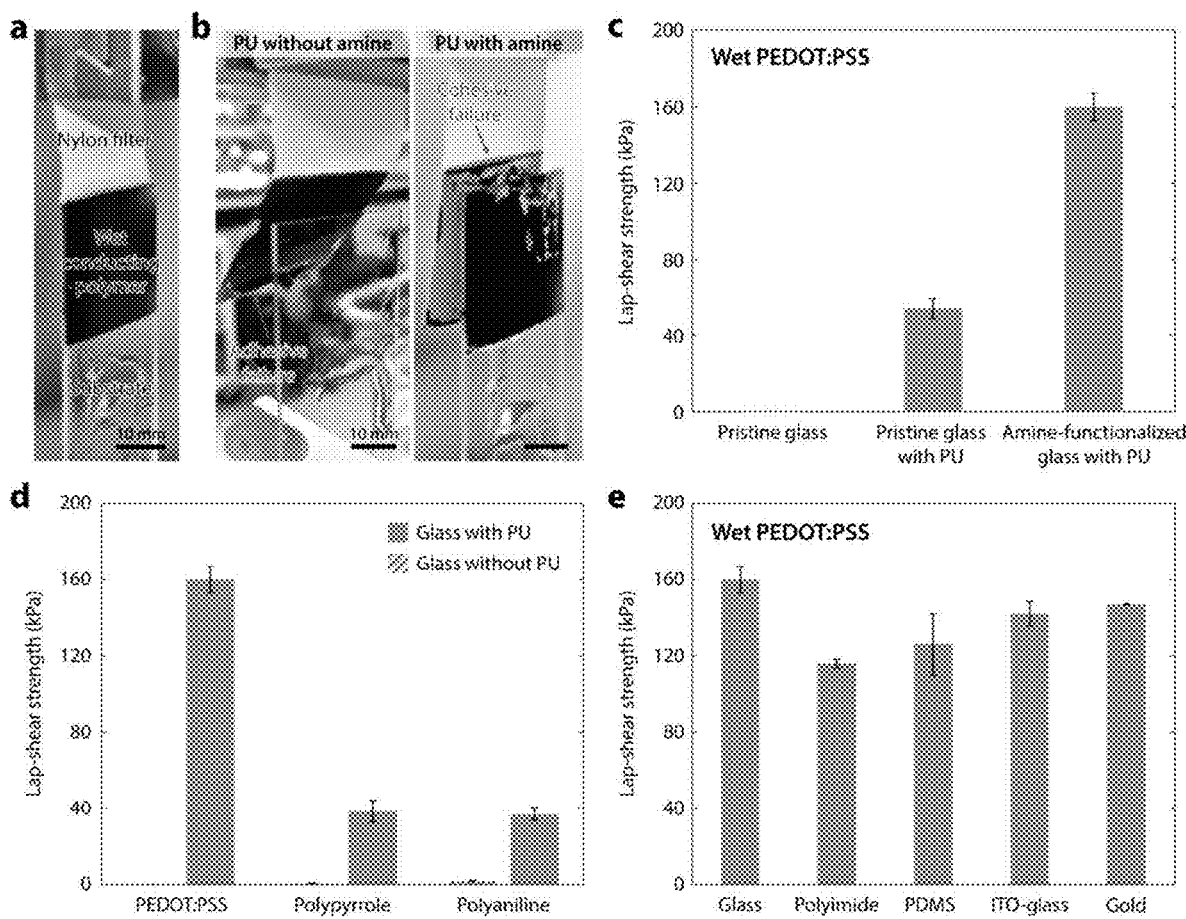
FIGS. 6A-E illustrate various adhesion properties of conducting polymers on diverse substrates, in accordance with embodiments of the present invention. with FIG. 6A showing a typical lap-shear testing setup, FIG. 6B showing an adhesive failure for a wet PEDOT:PSS on a PU-coated glass substrate without primary amine functionalization (left) and cohesive failure with primary amine functionalization (right), FIG. 6C graphically illustrating lap-shear strength of a wet PEDOT:PSS on pristine glass, pristine glass with a PU adhesion layer, and an amine-functionalized glass with a PU adhesion layer, FIG. 6D graphically illustrating lap-shear strength of various wet conducting polymers (PEDOT:PSS, PPy, PAni) on a pristine glass without a PU adhesion layer and on an amine-functionalized glass with a PU adhesion layer, and FIG. 6E graphically illustrating lap-shear strength of wet PEDOT:PSS on various PU-coated amine-functionalized insulating and conductive substrates. Values in FIGS. 6C-E represent the mean and the error bars represent the s.d. of measured values (n=3).

To evaluate the bonding/adhesion strength of wet conducting polymers on diverse substrates, lap-shear tests were performed to measure interfacial shear strength (see FIGS. 6A-E). A typical lap-shear testing sample and setup is illustrated in FIG. 6A. As shown, a wet PEDOT:PSS is sandwiched between a hydrophilic microporous nylon filter (pore size, 1 μm) and a PU-coated substrate. Hydrophilic microporous nylon filters were used as a backing for the lab-shear tests due to two advantageous features: (i) the nylon filters have a high mechanical stiffness (Young's modulus >1 GPa), which can prevent undesirable deformation of the wet conducting polymers during the measurements, and (ii) hydrophilicity and microporosity of the nylon filters allow infiltration of conducting polymers and subsequent reliable mechanical integration during the lap-shear tests. As demonstrated, wet PEDOT:PSS on the PU-coated glass substrate exhibited a high shear strength (>50 kPa) while the wet PEDOT:PSS on the pristine glass substrate (without a PU adhesion layer and amine functionalization) showed very low shear strength (0.08 kPa) and easily detached from the substrates (FIGS. 6B and 6C). Thus, the use of a hydrophilic PU adhesion layer according to the present invention is essential to providing strong adhesion of wet PEDOT:PSS on various substrates.

Figure 7:
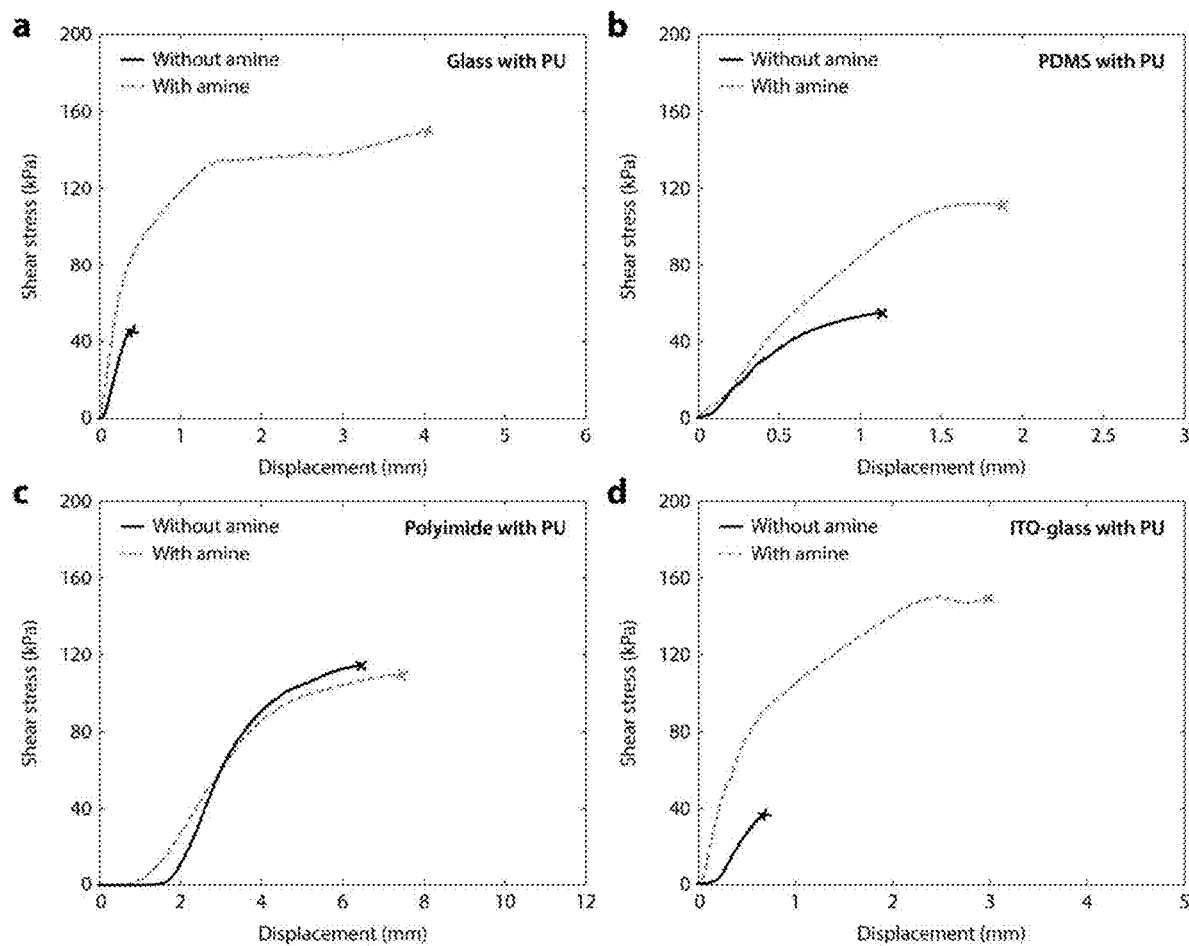
FIGS. 7A-D graphically illustrate displacement vs. shear stress curves for lap-shear tests of wet PEDOT:PSS on various PU-coated substrates with and without amine-functionalization, according to embodiments of the present invention, with FIG. 7A illustrating data for glass, FIG. 7B illustrating data for PDMS, FIG. 7C illustrating data for polyimide, and FIG. 7D illustrating data for ITO-glass.
Figure 8:
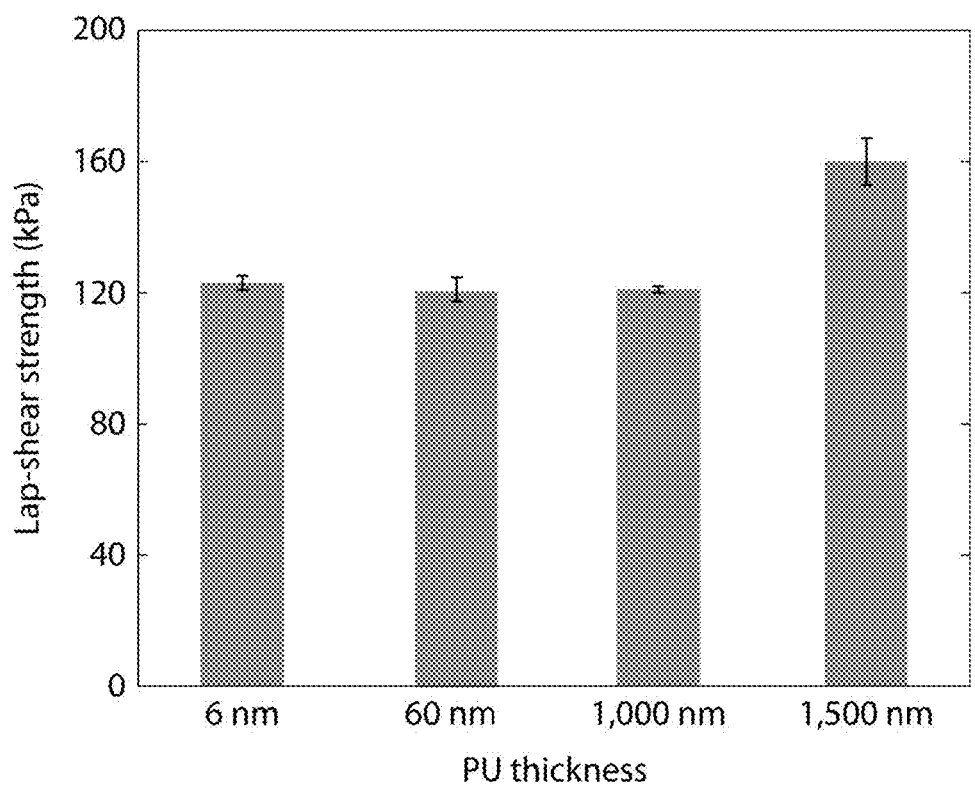
FIG. 8 graphically illustrates lap-shear strength vs. PU thickness for a wet PEDOT:PSS on a PU-coated amine-functionalized glass substrate, according to embodiments of the present invention. Values represent mean and the error bars represent the s.d. of measured values (n=3).

Surface functionalization of the substrates with primary amine groups was further analyzed in connection with adhesion performance. Shear strength and modes of failures were compared in the lap-shear tests for wet PEDOT:PSS on PU-coated glass substrates with and without primary amine functionalization. Notably, the wet PEDOT:PSS on the PU-coated amine-functionalized glass substrate exhibited cohesive failures (i.e., failure occurs within the wet PEDOT:PSS) while the wet PEDOT:PSS on the PU-coated pristine (i.e., no amine-functionalization) glass substrate demonstrated adhesive failures (i.e., failure occurs at the PU adhesion layer) (FIG. 6B). This demonstrated that amine-functionalization further enhanced the adhesive strength. Moreover, the PU-coated amine-functionalized glass substrates provided much higher shear strength than the PU-coated pristine (i.e., no amine-functionalization) glass substrates (160 kPa vs. 54 kPa) (FIGS. 6C and 7). Based on these results, primary amine functionalization of the substrate and the resultant improved adhesion between the PU adhesion layer and the substrate are important factors in achieving strong adhesion. It was also determined that the PU adhesion layer provides strong adhesion of wet PEDOT:PSS (shear strength over 120 kPa) consistently over a wide range of PU adhesion layer thickness (6 nm to 1,500 nm) (FIG. 8).

Figure 9:
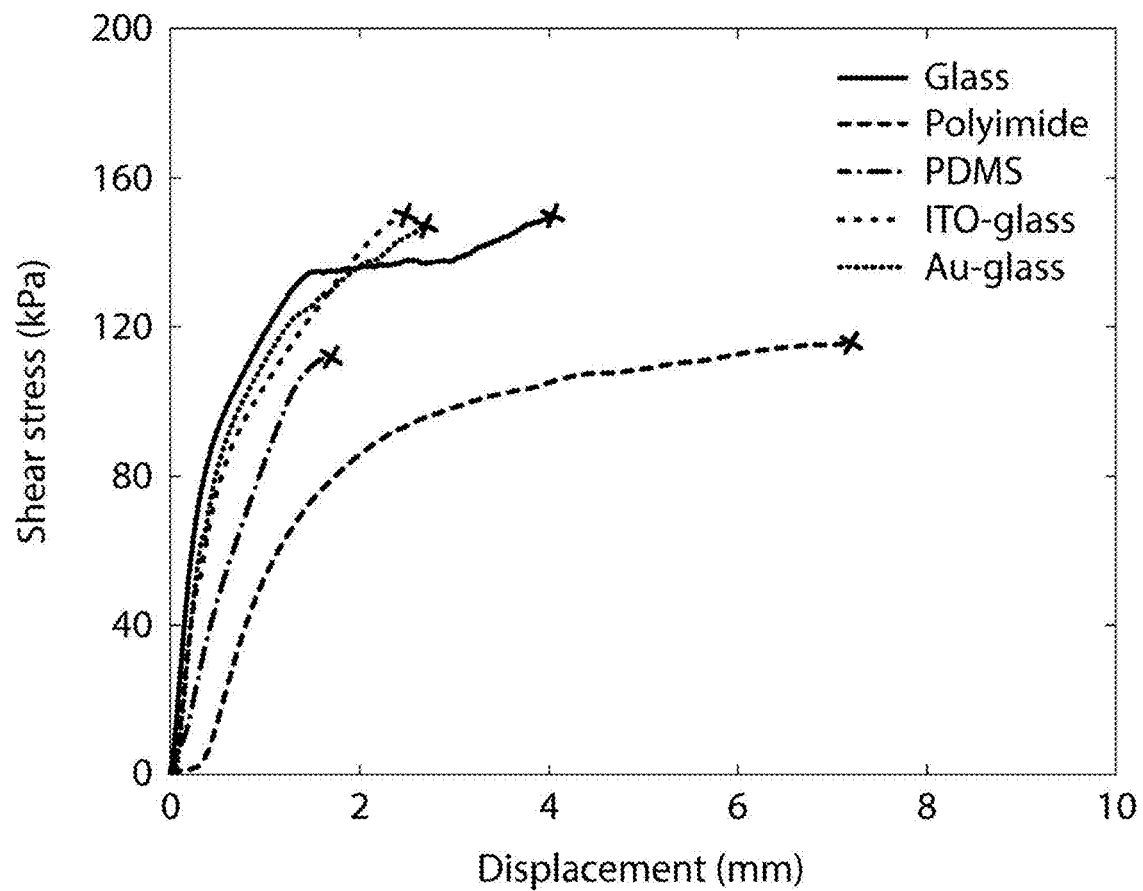
FIG. 9 graphically illustrates displacement vs. shear stress curves for a lap-shear tests of a wet PEDOT:PSS on various PU-coated amine-functionalized substrates, according to embodiments of the present invention.

Thus, the present invention provides flexibility in processing and material options. As a result, the present invention is generally applicable for various wet conducting polymers as well as a wide range of insulating and conductive substrates for bioelectronic devices (FIGS. 6D and 6E). As demonstrated, the solvent-casted wet PEDOT:PSS, PPy, and PAni on amine-functionalized glass with a PU adhesion layer provided significantly higher shear strength than the same materials on pristine (i.e., no amine-functionalization) glass without a PU adhesion layer (160 kPa vs. 0.1 kPa for PEDOT:PSS; 39 kPa vs. 0.4 kPa for PPy; 37 kPa vs. 1.9 kPa for PAni) (FIG. 6D). The present invention also enables strong interfacial adhesion of wet PEDOT:PSS on diverse amine-functionalized insulating and conductive substrates including, but not limited to, glass (shear strength, 160 kPa), polyimide (shear strength, 116 kPa), PDMS (shear strength, 111 kPa), ITO-glass (shear strength, 149 kPa), and gold (shear strength, 146 kPa) (FIGS. 6E and 9). As such, the present invention achieves strong adhesion of conducting polymers using previously inaccessible fabrication methods and/or upon substrates that could not previously be successfully adhered to utilizing existing techniques.

Example 2: Mechanical and Electrical Properties of Adhesion Interface

In bioelectronic devices and their applications, it is highly desirable that adhesion interfaces between the conducting polymers and the substrates provide robust interfacial adhesion in wet environments, while not affecting mechanical and electrical properties of the conducting polymer and devices.

Figure 10:
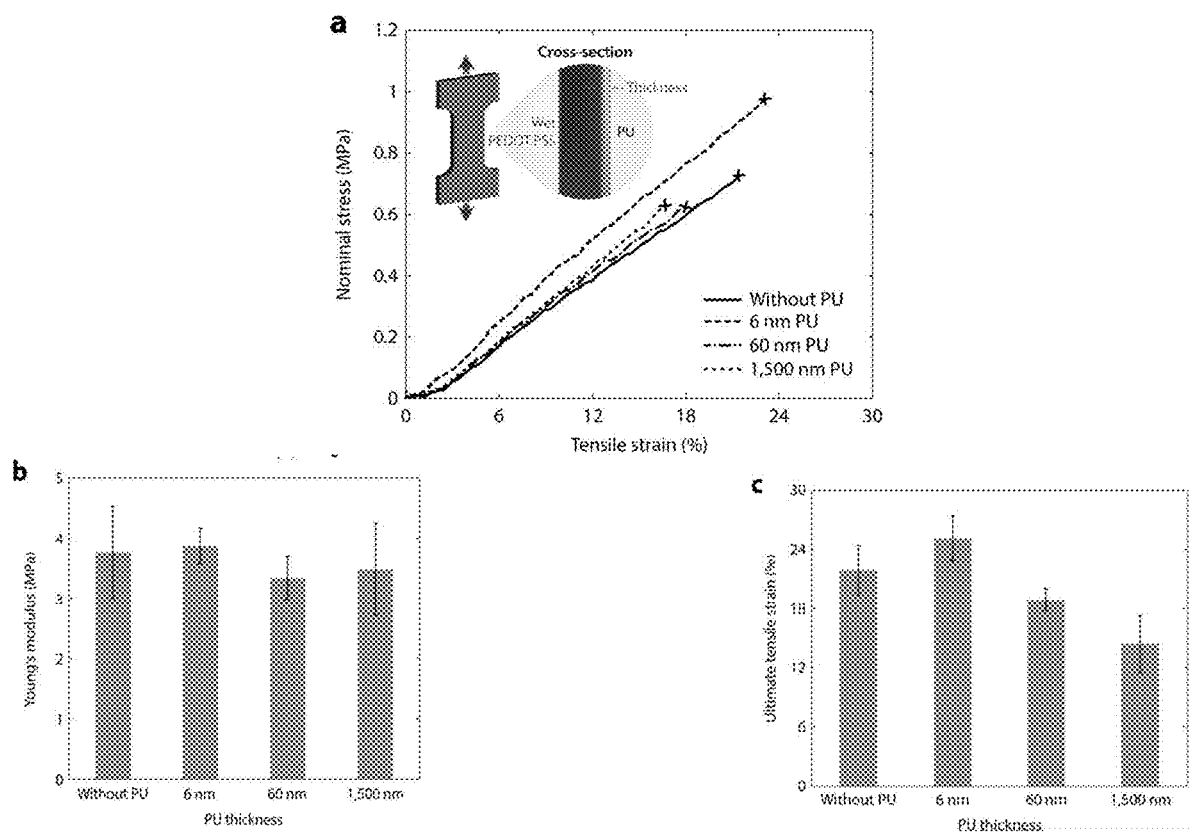
FIGS. 10A-C graphically illustrate mechanical properties of wet PEDOT:PSS with varying PU adhesion layer thickness, according to embodiments of the present invention, with FIG. 10A illustrating nominal stress vs. nominal tensile strain curves, FIG. 10B illustrating Young's moduli, and FIG. 10C illustrating ultimate tensile strain. Values in b,c represent mean and the error bars represent the s.d. of measured values (n=3).

In order to assess the effect of a PU adhesion layer on the properties of conducting polymers in a wet environment, the mechanical and electrical properties of the adhesion interfaces were analyzed using PEDOT:PSS as a representative conducting polymer (FIGS. 10A-C and 11A-D). To quantitatively evaluate the effect of a PU adhesion layer on the mechanical properties of wet PEDOT:PSS, tensile tests of the solvent-casted wet PEDOT:PSS in PBS were conducted without a PU adhesion layer and with varying thickness PU adhesion layers (FIG. 10A). Young's moduli of the wet PEDOT:PSS with varying thickness of PU layers (6 nm to 1,500 nm) exhibit negligible difference compared to the wet PEDOT:PSS without a PU layer (FIG. 10B). Ultimate tensile strain of the wet PEDOT:PSS is not affected by the relatively thin PU layers (6 nm and 60 nm) while the thick PU layer (1,500 nm) reduces the stretchability of wet PEDOT:PSS (from 23% to 14% strain), potentially due to the mechanical mismatch between the PU layer and the wet PEDOT:PSS (FIG. 10C). Hence, the relatively thin PU adhesion layer (<60 nm) was shown to provide strong adhesion of wet PEDOT:PSS (FIG. 8) without compromising the mechanical properties of the wet PEDOT:PSS. Generally, thicknesses on the nanometer scale (at least up to about 100 nm) are expected to provide such strong adhesion without compromising the mechanical properties of the wet PEDOT:PSS. While thicker PU adhesion layers (on the order of 1,500 nm) provides strong adhesion, some compromise in stretchability results, thus possibly limiting the use of thicker PU adhesion layers in some applications which require stretchability. As a general guideline, the PU adhesion layer is preferably much thinner than the conducting polymer thickness (on the order of <5%) to avoid undesirable influence on material properties.

Figure 11:
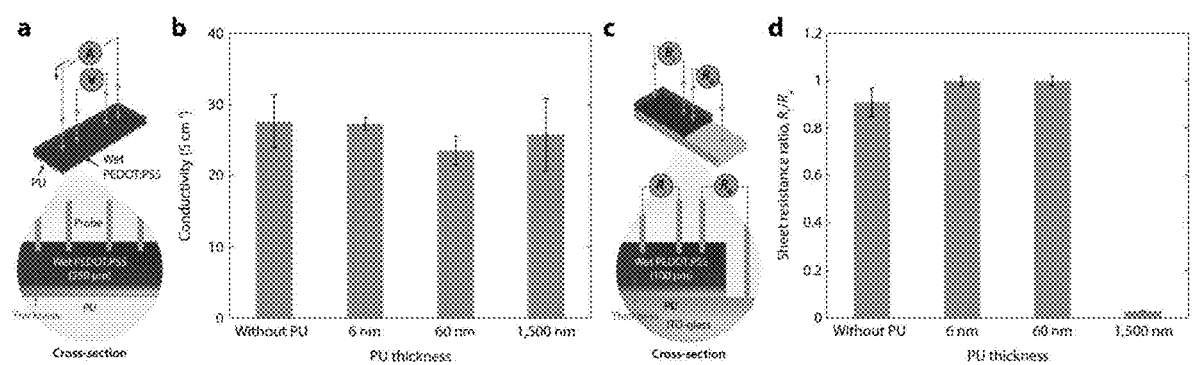
FIGS. 11A-D schematically and graphically illustrate electrical properties of adhesion interfaces with varying PU adhesion layer thickness, according to embodiments of the present invention, with FIG. 11A schematically illustrating for electrical conductivity measurement by a standard 4-point probe method, FIG. 11B graphically illustrating conductivity with varying PU adhesion layer thickness, FIG. 11C schematically illustrating electrical property measurements of adhesion interfaces between wet PEDOT:PSS and the underneath PU-coated ITO-glass electrodes, and FIG. 11D graphically illustrating sheet resistance ratio $R_t/R_{it}$ between the wet PEDOT:PSS and the underneath PU-coated ITO-glass electrodes with varying PU adhesion layer thickness. Values in b,d represent mean and the error bars represent the s.d. of measured values (n=3).

The electrical properties of adhesion interfaces were analyzed to evaluate the effect of a PU adhesion layer on the electrical performance of adhered wet conducting polymers. The electrical conductivity of wet PEDOT:PSS was measured without a PU adhesion layer and with varying thickness of PU adhesion layers by the standard 4-point probe method in deionized water (FIG. 11A). Electrical conductivity of the wet PEDOT:PSS exhibits small (<10%) or negligible reduction over a wide range of PU thickness (6 nm to 1,500 nm), indicating an insignificant effect of the PU adhesion layer on the electrical properties of wet PEDOT:PSS (FIG. 11B). To determine the effect of a PU adhesion layer on the electrical connections between the wet PEDOT:

PSS and the underneath electrodes, the sheet resistance was measured between the wet PEDOT:PSS and the PU-coated amine-functionalized ITO-glass substrates (FIG. 11C). Notably, the thinner PU adhesion layers (6 nm and 60 nm) provided negligible changes in sheet resistance between the wet PEDOT:PSS and the ITO-glass electrode (i.e., sheet resistance ratio Ri/Rii~1), while the thicker PU adhesion layer (1,500 nm) resulted in substantially increased interfacial resistance (i.e., Ri/Rii<<1) (FIG. 11D). While PEDOT: PSS can diffuse and form a gradient of interpenetrating layer toward the hydrophilic PU up to ~50 μm thickness (FIG. 5) the electrical impedance of the resultant interpenetrating layer is proportional to the thickness of the PU adhesion layer. Hence, the thicker PU adhesion layer (e.g., on the order of 1,500 nm) can substantially increase the interfacial resistance between the wet conducting polymer and the underlying electrode even with the presence of interpenetrated conducting polymer throughout the PU adhesion layer, whereas thinner PU adhesion layers (i.e., nanometer-thick) can provide low interfacial resistance.

Figure 5:
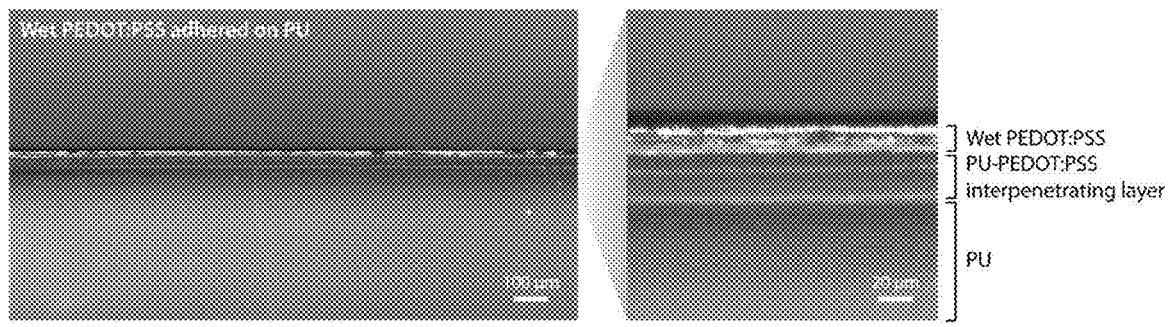
FIG. 5 illustrates cross-sectional optical microscope images of a wet PEDOT:PSS on a PU-coated substrate, in accordance with an embodiment of the present invention.
Figure 12:
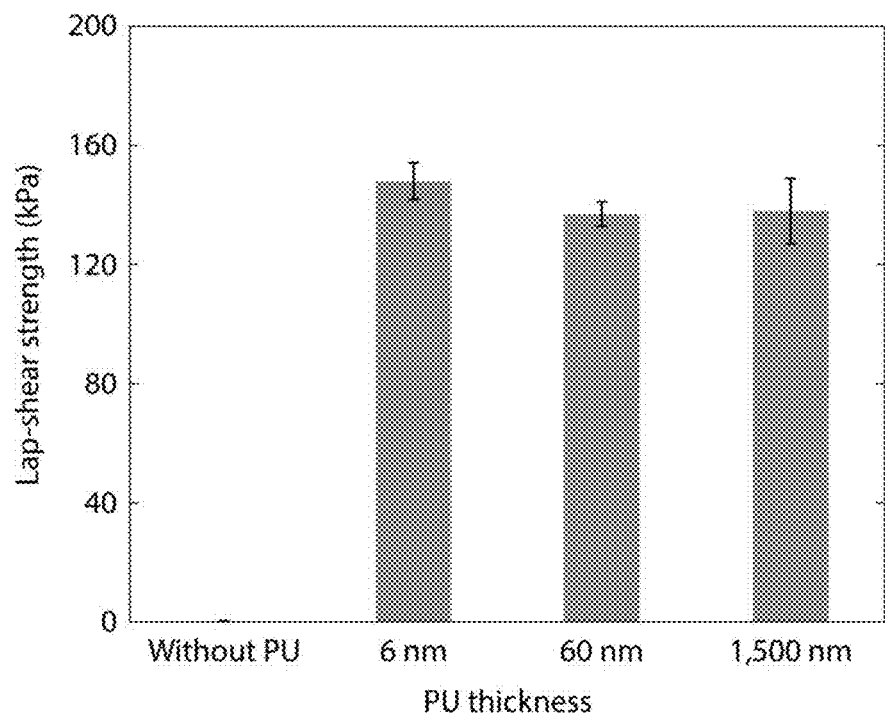
FIG. 12 graphically illustrates lap-shear strength vs. PU thickness for wet PEDOT:PSS on a PU-coated amine-functionalized ITO-glass substrate of varying thickness, according to embodiments of the present invention. Values represent mean and the error bars represent the s.d. of measured values (n=3).

These results indicate that a thinner PU adhesion layer can offer strong adhesion without affecting the electrical connection between the wet PEDOT:PSS and the underneath electrode (FIGS. 11D and 12) while a thicker PU adhesion layer acts as an electrically insulating layer (FIGS. 5 and 11D). For applications that require strong adhesion of wet conducting polymers with insulating interface, a thicker PU adhesion layer (e.g., on the order of about 1 μm/about 1,000 nm) may find particular utility.

Example 3: Electrochemical and Mechanical Stability of Adhesion Interface

Figure 13:
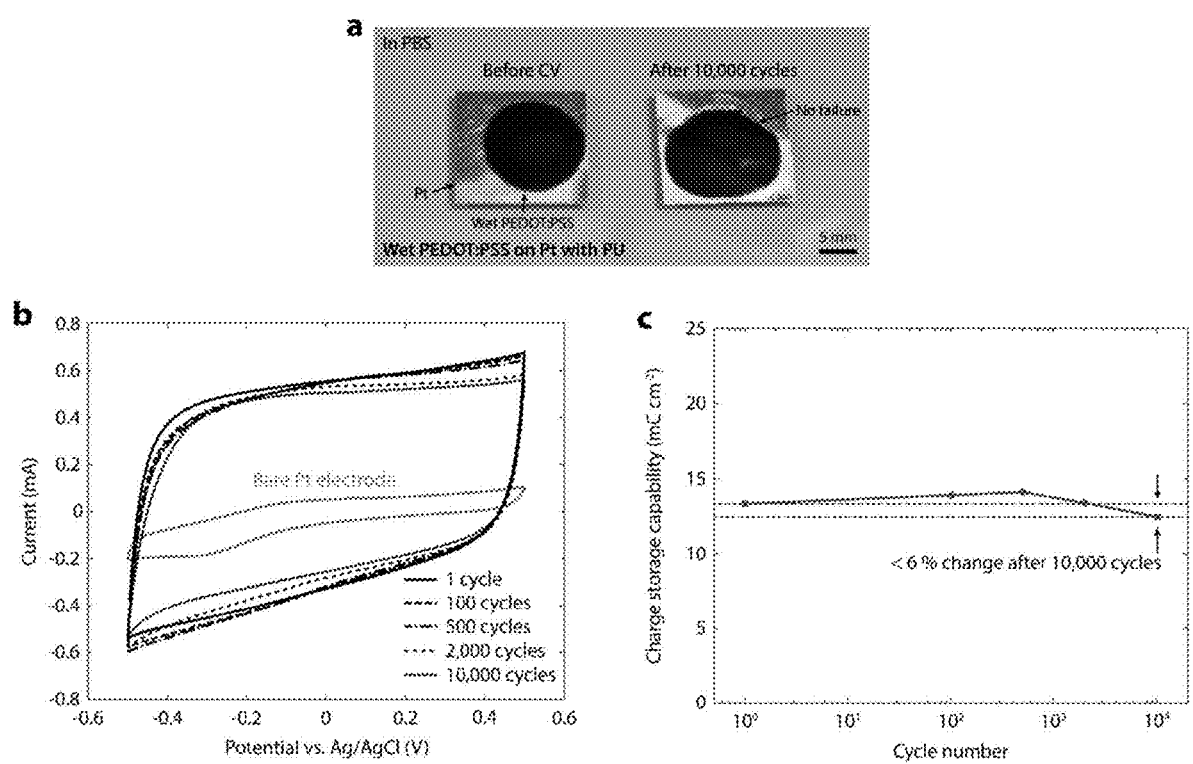
FIGS. 13A-C illustrate the electrochemical stability of wet PEDOT:PSS on platinum, according to embodiments of the present invention, with FIG. 13A showing images of a wet PEDOT:PSS on PU-coated amine-functionalized Pt electrodes before and after 10,000 CV charging and discharging cycles in PBS, FIG. 13B graphically illustrating long-term CV curves for the wet PEDOT:PSS on PU-coated amine-functionalized Pt electrodes in PBS, and FIG. 13C graphically illustrating measured CSC vs. CV cycle number for wet PEDOT:PSS on PU-coated amine-functionalized Pt electrodes in PBS.

To determine electrochemical stability of the adhesion interface, stability and electrochemical properties of the wet PEDOT:PSS on the PU-coated amine-functionalized platinum electrodes were analyzed via cyclic voltammetry (CV) tests in PBS (FIG. 13). The wet PEDOT:PSS on the PU-coated platinum electrodes remained intact without any observable interfacial failures after 10,000 cycles of CV charging and discharging cycles (FIG. 13A). Moreover, the CV curves show a small change over 10,000 CV charging and discharging cycles with less than a 6% decrease in charge storage capability (CSC) after 10,000 CV cycles, demonstrating superior electrochemical stability of the adhesion interface by the PU adhesion layer (FIGS. 13B-C).

Figure 14:
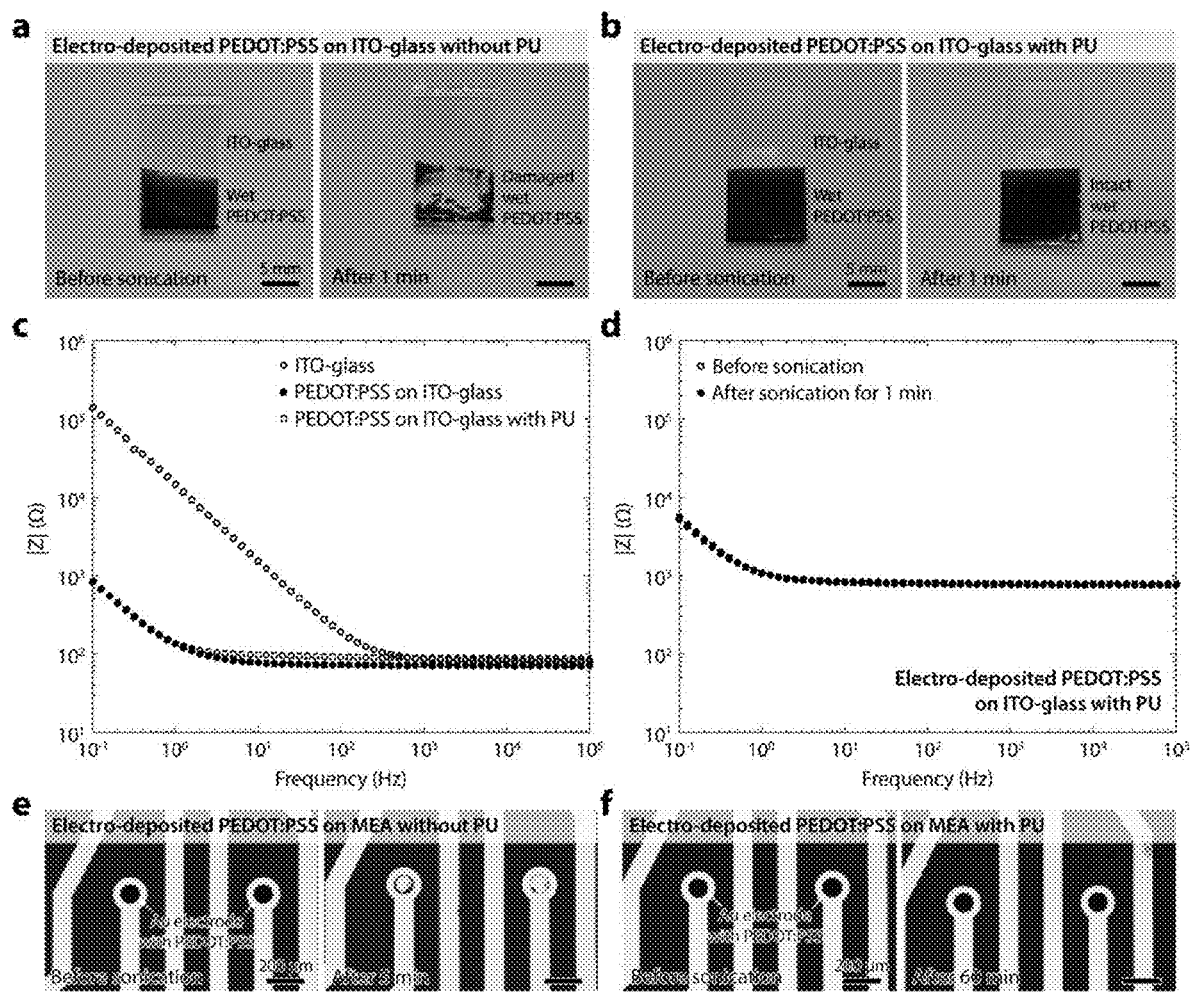
FIGS. 14A-F illustrate the stability of adhesion of wet PEDOT:PSS under prolonged ultrasonication, according to embodiments of the present invention, with FIG. 14A showing images of electro-deposited wet PEDOT:PSS on pristine ITO-glass without a PU adhesion layer before and after ultrasonication for 1 min, FIG. 14B showing images of electro-deposited wet PEDOT:PSS on PU-coated amine-functionalized ITO-glass before and after 1 min ultrasonication, FIG. 14C graphically illustrating EIS curves for the pristine ITO-glass, the electro-deposited wet PEDOT:PSS on the pristine ITO-glass, and the electro-deposited wet PEDOT:PSS on the PU-coated amine-functionalized ITO-glass, FIG. 14D graphically illustrating EIS curves for the electro-deposited wet PEDOT:PSS on the PU-coated amine-functionalized ITO-glass before and after ultrasonication for 1 min, FIG. 14E showing optical microscope images of electro-deposited wet PEDOT:PSS on the pristine MEA with Au electrodes before and after ultrasonication for 5 min, and FIG. 14F showing optical microscope images of electro-deposited wet PEDOT:PSS on PU-coated amine-functionalized MEA with Au electrodes before and after ultrasonication for 60 min.
Figure 15:
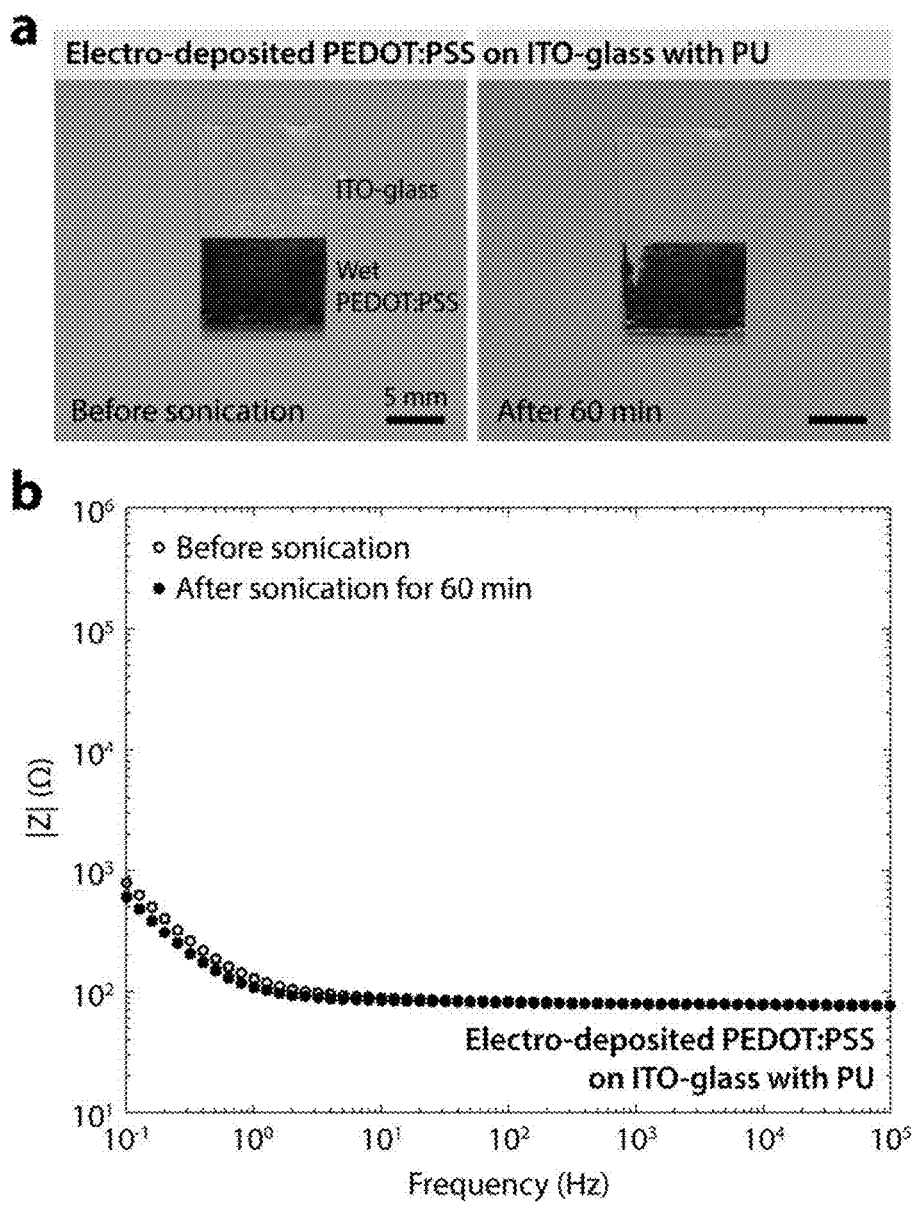
FIGS. 15A-B illustrate the stability of the wet PEDOT:PSS on PU-coated amine-functionalized ITO-glass substrates under ultrasonication, according to embodiments of the present invention, with FIG. 15A showing images of electro-deposited wet PEDOT:PSS on a PU-coated amine-functionalized ITO-glass substrates before and after ultrasonication for 60 min, and FIG. 15B graphically illustrating EIS curves for electro-deposited wet PEDOT:PSS on PU-coated amine-functionalized ITO-glass before and after ultrasonication for 60 min.

Mechanical stability of the adhesion interface was further analyzed by characterizing the degree of interfacial failures and electrical properties of the electro-deposited wet PEDOT:PSS on the PU-coated electrodes under prolonged ultrasonication in PBS (FIGS. 14A-F). The electro-deposited wet PEDOT:PSS on the pristine ITO-glass (without a PU adhesion layer and amine functionalization) underwent severe damage and complete interfacial delamination after ultrasonication for 1 min due to weak adhesion between the wet PEDOT:PSS and the substrate (FIG. 14A). On the other hand, the electro-deposited PEDOT:PSS on the PU-coated amine-functionalized ITO-glass remained intact after ultrasonication for 1 min and exhibited a negligible degree of damage even after 60 min of continuous ultrasonication (FIGS. 14B and 15A). Notably, the presence of PU adhesion layers did not alter the favorable electrical enhancement from the electro-deposited PEDOT:PSS on the ITO-glass electrodes (i.e. lower impedance than bare ITO-glass electrode in the low frequency region) (FIG. 14C) while providing superior robustness and stability against severe mechanical stimuli such as prolonged ultrasonication (FIGS. 14D and 15B). Furthermore, the solvent-casted wet PEDOT: PSS on the PU-coated amine-functionalized PDMS substrate was shown to withstand and remain intact without interfacial failure after 10,000 cycles of bending deformations (the radius of curvature ~2 mm) in PBS.

It was further demonstrated that the present invention is readily applicable for commercially-available bioelectronic devices, such as multielectrode arrays (MEA), thereby offering robust integration of wet PEDOT:PSS with superior stability (FIGS. 14E-F). While electro-deposition of PEDOT:PSS is frequently adopted for multielectrode arrays to improve electrical properties (e.g., low impedance, high charge injection capacity), the poor long-term stability of electro-deposited PEDOT:PSS on microelectrodes in wet physiological environments has significantly limited their utility (See Venkatraman, S. et al. In vitro and in vivo evaluation of PEDOT microelectrodes for neural stimulation and recording. *IEEE Transactions on Neural Systems Rehabilitation Engineering* 19, 307-316 (2011); Ouyang, L. et al. Enhanced PEDOT adhesion on solid substrates with electrografted P (EDOT-NH2). *Science Advances* 3, e1600448 (2017); Boehler, C., Oberueber, F., Schlabach, S., Stieglitz, T. & Asplund, M. Long-term stable adhesion for conducting polymers in biomedical applications: IrOx and nanostructured platinum solve the chronic challenge. *ACS Applied Materials & Interfaces* 9, 189-197 (2016); Wei, B., Liu, J., Ouyang, L., Kuo, C.-C. & Martin, D. C. Significant enhancement of PEDOT thin film adhesion to inorganic solid substrates with EDOT-acid. *ACS Applied Materials & Interfaces* 7, 15388-15394 (2015)).

It was found that the electro-deposited wet PEDOT:PSS on a bare MEA with Au electrodes (electrode diameter, 100 μm) was completely separated from the electrode surfaces via delamination failures after ultrasonication for 5 min (FIG. 14A). In contrast, according to the present invention, an electro-deposited wet PEDOT:PSS on a PU-coated amine functionalized MEA with Au electrodes exhibited no observable damage and remained intact even after ultrasonication for 60 min. Thus, the present invention clearly provides superior stability and strong adhesion even in wet environments (FIG. 14F).

Example 4: Strong Adhesion Conducting Polymers on Various Bioelectronic Devices

Figure 16:
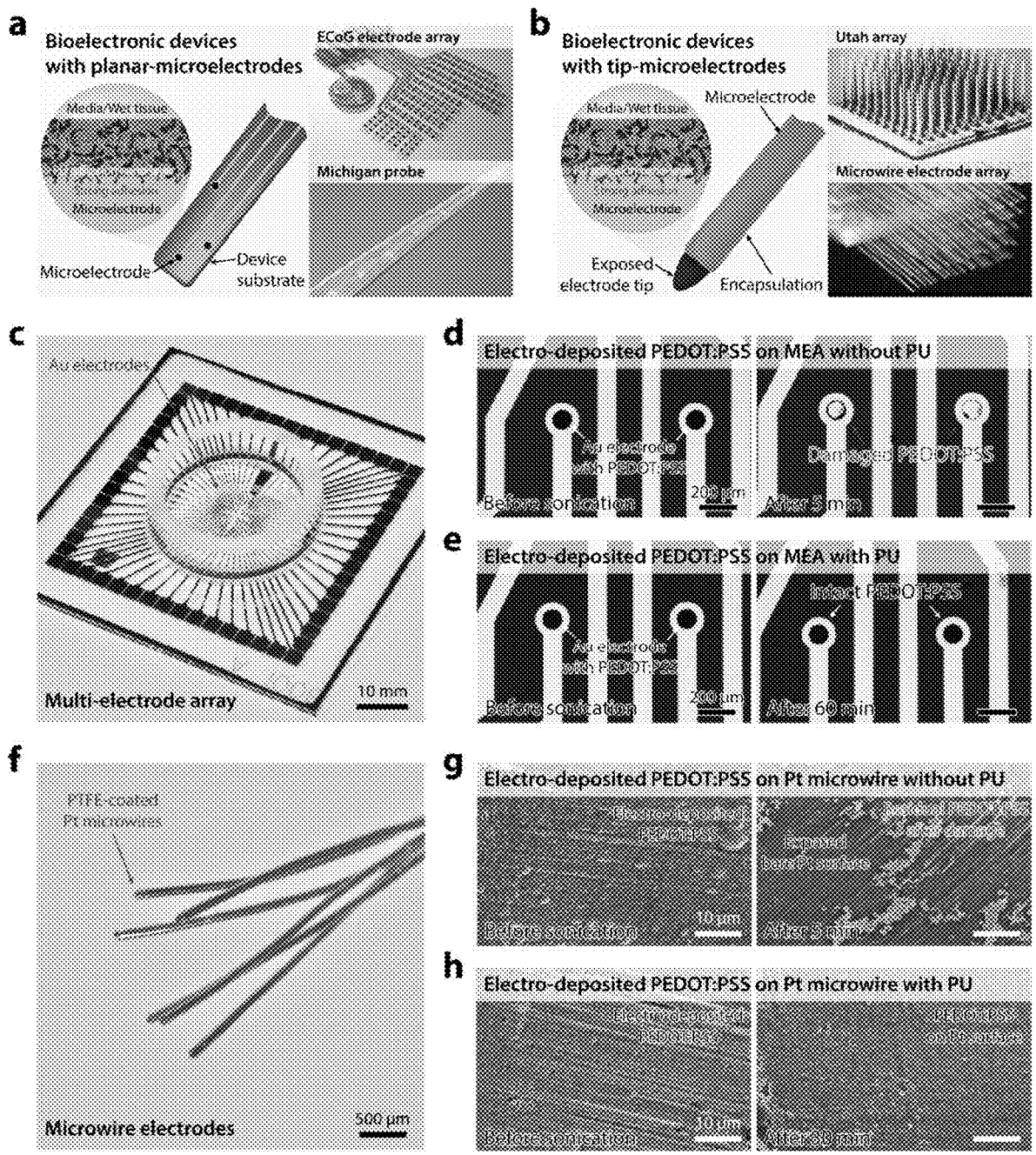
FIG. 16A-H illustrate the strong adhesion of wet conducting polymers on various bioelectronic devices according to embodiments of the present invention, with FIG. 16A illustrating adhesion of wet conducting polymers for bioelectronic devices with planar-microelectrodes, FIG. 16B illustrating the adhesion of wet conducting polymers for bioelectronic devices with tip-microelectrodes, FIG. 16C illustrating a commercially-available micro-electrode array (MEA) with Au electrodes, FIG. 16D showing optical microscope images of the electro-deposited wet PEDOT:PSS on a pristine MEA before and after ultrasonication for 5 min, FIG. 16E showing optical microscope images of electro-deposited wet PEDOT:PSS on a PU-coated amine-functionalized MEA before and after ultrasonication for 60 min, FIG. 16F showing an image of commercially-available PTFE-coated Pt microwire electrodes, FIG. 16G showing SEM images of electro-deposited PEDOT:PSS on a pristine Pt microwire before and after ultrasonication for 5 min, and FIG. 16H showing SEM images of electro-deposited PEDOT:PSS on a PU-coated amine-functionalized Pt microwire before and after ultrasonication for 30 min.

While electro-deposited PEDOT:PSS has been intensively studied to improve the properties of various bioelectrodes (e.g., low impedance, high charge injection capacity, low rigidity), the poor long-term stability of electro-deposited PEDOT:PSS on bioelectrodes in wet physiological environments is one major hurdle that significantly limits their utility in practice. The present invention's capability of forming strong, conductive, and mechanically and electro-chemically stable adhesion between conducting polymers and diverse substrates provides a mechanism for readily electro-depositing conducting polymers on various existing bioelectronic devices, achieving high robustness in wet physiological conditions (FIGS. 16A-H). Existing bioelectronic devices can largely be classified into two categories based on the configurations of their electrodes. In the first category, bioelectronic devices, such as electrocorticography (ECoG) arrays, Michigan probes and multi-electrode arrays (MEA), are formed of planar-microelectrodes on a device substrates to provide bioelectronic sensing or stimulation (FIG. 16A). In the second category, bioelectronic devices such as Utah arrays, microwire electrode arrays, and fiber probes, are formed of tip-microelectrodes at the endtips of the devices (FIG. 16B). In order to demonstrate the flexibility and ready applicability of the present invention to robustly integrate conducting polymers with various bioelectronic devices, commercially-available MEA with Au microelectrodes (FIG. 16C) and polytetrafluoroethylene (PTFE)-coated Pt microwire electrodes (FIG. 16F) were selected as representative examples for further analysis as bioelectronic devices with planar-microelectrodes and tip-microelectrodes, respectively.

Due to poor adhesion between the electro-deposited PEDOT:PSS and the electrode surface, the electro-deposited PEDOT:PSS on pristine MEA (i.e. no amine functional groups and no PU adhesion layer)(electrode diameter, 100 µm) was significantly damaged and nearly disappeared from the electrode surfaces after ultrasonication for 5 min in PBS (FIG. 16D). In contrast, the electro-deposited PEDOT:PSS on the PU-coated MEA in accordance with the present invention exhibited no observable damage and remained intact even after ultrasonication for 60 min in PBS, clearly demonstrating strong adhesion and superior stability of the PEDOT:PSS on PU-coated MEA (FIG. 16E). Similarly, the electro-deposited PEDOT:PSS on the pristine Pt microwire electrode (i.e. no amine functional groups and no PU adhesion layer) (wire diameter, 100 µm) showed significant damage with the pristine Pt surfaces exposed after ultrasonication for 5 min in PBS (FIG. 16G), while the electro-deposited PEDOT:PSS on the PU-coated Pt microwire electrode in accordance with the present invention exhibited no observable damage in the PEDOT:PSS even after ultrasonication for 30 min in PBS (FIG. 16H).

The present invention, thus, provides improved methods and materials for achieving strong adhesion of conducting polymers on diverse substrates, even when exposed to moisture and wet environments. The present invention uses a unique interfacial interpenetration approach through the use of a hydrophilic adhesion layer. The present method beneficially provides robust interfacial integration of various conducting polymers, such as PEDOT:PSS, PPy, and PAni, on a wide range of insulating and conductive substrates. Thus, the present invention can be effectively used for bioelectronic devices including glass, PDMS, polyimide, ITO, and gold, as well as commercially-available bioelectronic devices like MEA. The robust adhesion provided by the present materials and methods, even in wet environments where such adhesion typically breaks down, thus provide devices that can be used as implantable devices, in tissue engineering applications, as well as incorporation with a variety of engineering materials. The present invention provides an adhesion interface with superior adhesion performance (e.g., shear strength over 120 kPa) and remarkable electrochemical and mechanical stability without compromising the mechanical and electrical properties of the conducting polymers even in wet environments. The present method is compatible with various fabrication approaches for conducting polymers including, but not limited to, solvent-casting and electro-deposition and allows the use of commercially-accessible off-the-shelf materials (e.g., hydrophilic PU, conducting polymers), offering ready and broad utility and impact for existing as well as new bioelectronic devices. This present invention, thus, provides not only a simple method to solve a long-lasting challenge of robust integration of conducting polymers in bioelectronic devices, but also a general strategy to achieve strong adhesion between various hydrogels and substrates.

What is claimed is:

1. A device for use in a wet environment comprising:
   a substrate material fabricated of an insulating or conducting material, or a combination thereof, the substrate material having a top surface and a bottom surface;
   a hydrophilic adhesion layer disposed on at least a portion of one or more of the top surface and bottom surface, wherein the hydrophilic adhesion layer is configured to be applied at a nanoscale thickness between 1-1,500 nm;
   one or more conducting polymers adhered to at least a portion of one or more of the top surface and bottom surface of the substrate material via the hydrophilic adhesion layer, and
   an interpenetration layer formed through the hydrophilic adhesion layer, which acts as a bridging interface between the conducting polymer and the hydrophilic adhesion layer, providing strong interfacial adhesion,
   wherein the one or more conducting polymers are adhered with an adhesion strength that is substantially maintained when the implantable device is exposed to the wet environment.

2. The device of claim 1, wherein the hydrophilic adhesion layer is fabricated of at least one hydrophilic elastomer.

3. The device of claim 2, wherein the at least one hydrophilic elastomer is chosen from at least one polyvinyl alcohol (PVA), hydrophilic polyurethane, hydrophilic epoxy, hydrophilic silicone, latex, polyacrylamide, polyethylene glycol, polyhydroxy ethyl methacrylate, polyhydroxy ethyl acrylate, poly acrylic acid, copolymers thereof, and combinations thereof.

4. The device of claim 3, wherein the hydrophilic elastomer is a hydrophilic polyurethane.

5. The device of claim 1, further comprising one or more functional groups disposed between the substrate material and the hydrophilic adhesion layer.

6. The device of claim 5, wherein the one or more functional groups are selected from primary amine groups, carboxylic acid groups, thiol groups, vinyl groups, epoxide groups, succinimide groups, hydroxy groups, and combinations thereof.

7. The device of claim 5, wherein the hydrophilic adhesion layer is a polyurethane adhesion layer and the one or more functional groups are primary amine groups.

8. The device of claim 1, wherein the substrate is fabricated of materials selected from glass, silicon, polyimide, polycarbonate, perylene, polypropylene, polymethyl methacrylate (PMMA), polyethylene terephthalate (PETE), polydimethylsiloxane (PDMS), polyurethane, styrene-ethylene-butylene-styrene (SEBS),indium tin oxide (ITO), gold, platinum, titanium, titanium nitride, iridium, iridium oxide and combinations thereof.

9. The device of claim 1, wherein the substrate is a multielectrode array.

10. The device of claim 1, wherein the conducting polymers are selected from poly(3,4-ethylenedioxythiophene) (PEDOT), poly(3,4 ethylenedioxythiophene) polystyrene sulfonate (PEDOT:PSS), polythiophene, poly(p-phenylene sulfide), polypyrrole (PPy), polycarbazole, polyindole, polyazepine, polyaniline (PAni) and combinations thereof.

11. The device of claim 1, further comprising an interpenetrating layer disposed between the conducting polymer and the hydrophilic adhesion layer, wherein the interpenetrating layer is configured to possess a gradient from the conductive polymer to the hydrophilic adhesion layer.

12. The device of claim 10, wherein the interpenetrating layer is formed of interpenetrating networks between the conducting polymer and the hydrophilic adhesion layer.

13. The device of claim 1, wherein the device is a wearable or implantable device.

14. The device of claim 1, wherein the device is an implantable bioelectronic device.

15. A method for forming a device, which is disposed within or in contact with bodily fluids or which is used in a wet environment, comprising:
obtaining a substrate, the substrate having a top surface and a bottom surface;
disposing a hydrophilic adhesion layer on at least a portion of one or more of the top surface and bottom surface of the substrate, wherein the hydrophilic adhesion layer is configured to be applied at a nanoscale thickness between 1-1,500 nm;
adhering one or more conducting polymers to at least a portion of one or more of the top surface and bottom surface of the substrate via the hydrophilic adhesion layer; and
forming an interpenetration layer through the hydrophilic adhesion layer, which acts as a bridging interface between the conducting polymer and the hydrophilic adhesion layer, providing strong interfacial adhesion,
wherein the one or more conducting polymers are adhered with an adhesion strength that is substantially maintained when the implantable device is exposed to the wet environment.

16. The method of claim 15, wherein the hydrophilic adhesion layer is fabricated of at least one hydrophilic elastomer.

17. The method of claim 16, wherein the at least one hydrophilic elastomer is chosen from at least one polyvinyl alcohol (PVA), hydrophilic polyurethane, hydrophilic epoxy, hydrophilic silicone, latex, polyacrylamide, polyethylene glycol, polyhydroxy ethyl methacrylate, polyhydroxy ethyl acrylate, poly acrylic acid, copolymers thereof, and combinations thereof.

18. The method of claim 17, wherein the hydrophilic elastomer is a hydrophilic polyurethane.

19. The method of claim 15, further comprising:
prior to disposing the hydrophilic adhesion layer, functionalizing the substrate with one or more functional groups.

20. The method of claim 19, wherein the one or more functional groups are selected from primary amine groups, carboxylic acid groups, thiol groups, vinyl groups, epoxide groups, succinimide groups, hydroxy groups, and combinations thereof.

21. The method of claim 19, wherein the hydrophilic adhesion layer is a polyurethane adhesion layer and the one or more functional groups are primary amine groups.

22. The method of claim 15, wherein the substrate is fabricated of insulating materials, conducting materials, or combinations thereof.

23. The method of claim 15, wherein the substrate is fabricated of materials selected from glass, silicon, polyimide, polycarbonate, perylene, polypropylene, polymethyl methacrylate (PMMA), polyethylene terephthalate (PETE), polydimethylsiloxane (PDMS), polyurethane, styrene-ethylene-butylene-styrene (SEBS), indium tin oxide (ITO), gold, platinum, titanium, titanium nitride, iridium, iridium oxide and combinations thereof.

24. The method of claim 15, wherein the substrate is a multielectrode array.

25. The method of claim 15, wherein the conducting polymers are selected from poly(3,4-ethylenedioxythiophene) (PEDOT), poly(3,4-ethylenedioxythiophene) polystyrene sulfonate (PEDOT:PSS), polythiophene, poly(p-phenylene sulfide), polypyrrole (PPy), polycarbazole, polyindole, polyazepine, polyaniline (PAni) and combinations thereof.

26. The method of claim 15, wherein the conducting polymers are adhered by solvent-casting or electro-deposition methods.

27. The method of claim 15, wherein the hydrophilic adhesion layer is disposed on the substrate material by spin-coating, spray-coating, dip-coating, or combinations thereof.

28. The method of claim 15, wherein the step of adhering one or more conducting polymers comprises using a precursor solution containing moisture to trigger swelling of the hydrophilic adhesion layer, and wherein the method further comprises, allowing the hydrophilic adhesion layer to swell, and allowing the conducting polymer to diffuse into and through the hydrophilic e adhesion layer to form an interpenetrating layer.

29. The method of claim 28, wherein the interpenetrating layer is formed between the conducting polymer and the hydrophilic adhesion layer.

30. The method of claim 28, wherein the interpenetrating layer is formed by interpenetrating networks between the conducting polymer and the hydrophilic adhesion layer.

31. The method of claim 28, wherein the interpenetrating layer is a bridging interface providing increased interfacial adhesion between the conducting polymer and the hydrophilic adhesion layer coated substrate in the wet environment.

* * * * *